United States Patent
Larsson et al.

(10) Patent No.: US 11,559,614 B2
(45) Date of Patent: Jan. 24, 2023

(54) BREAST SHIELD

(71) Applicant: MEDELA HOLDING AG, Baar (CH)

(72) Inventors: Michael Larsson, Zug (CH); Erich Pfenniger, Ebikon (CH); Mario Rigert, Buchrain (CH); Sebastian Höner, Thalwil (CH); Peter Vischer, Küssnacht Am Rigi (CH); Peter Edwin Hartmann, Gooseberry Hill (AU)

(73) Assignee: MEDELA HOLDING AG, Baar (CH)

( * ) Notice: Subject to any disclaimer, the term of this patent is extended or adjusted under 35 U.S.C. 154(b) by 821 days.

(21) Appl. No.: 16/329,841

(22) PCT Filed: Sep. 2, 2016

(86) PCT No.: PCT/EP2016/070742
§ 371 (c)(1),
(2) Date: Mar. 1, 2019

(87) PCT Pub. No.: WO2018/041365
PCT Pub. Date: Mar. 8, 2018

(65) Prior Publication Data
US 2019/0240386 A1    Aug. 8, 2019

(51) Int. Cl.
*A61M 1/06* (2006.01)
*A61M 1/00* (2006.01)

(52) U.S. Cl.
CPC .............. *A61M 1/064* (2014.02); *A61M 1/06* (2013.01); *A61M 1/066* (2014.02); *A61M 1/75* (2021.05);
(Continued)

(58) Field of Classification Search
CPC ........ A61M 1/06; A61M 1/064; A61M 1/066; A61M 2205/0216; A61M 2205/13;
(Continued)

(56) References Cited

U.S. PATENT DOCUMENTS

| 4,607,596 A | 8/1986 | Whittlestone et al. |
| 7,201,735 B2 | 4/2007 | Atkin et al. |

(Continued)

FOREIGN PATENT DOCUMENTS

| CN | 201469750 U | 5/2010 |
| CN | 102665783 A | 9/2012 |

(Continued)

OTHER PUBLICATIONS

Chinese Search Report for Application No. 201680088886.7, dated Sep. 25, 2020.
(Continued)

*Primary Examiner* — Brandy S Lee
(74) *Attorney, Agent, or Firm* — Marshall, Gerstein & Borun LLP

(57) ABSTRACT

A method for operating a breastpump unit for expression of human breastmilk and various breast shields for use in this method allow a maximum pumping performance and a minimum pumping duration per pumping session. The breast shield has an inner chamber for receiving a nipple of the breast and also at least one outer chamber which at least partially surrounds the nipple. The inner chamber is subjected to a constant pressure and the at least one outer chamber is subjected to a pulsating pressure.

20 Claims, 15 Drawing Sheets

(52) U.S. Cl.
CPC . *A61M 2205/0216* (2013.01); *A61M 2205/13* (2013.01); *A61M 2205/3306* (2013.01)

(58) Field of Classification Search
CPC ........ A61M 2205/3306; A61M 1/0037; A61M 1/75; A61M 1/285; A61M 1/3653; A61M 39/0247; A61M 39/22; A61M 5/427; A61M 1/3659; A61M 1/3661; A61M 2039/0018; A61M 2039/0258; A61M 2039/027; A61M 2039/0273; A61M 2039/0285; A61M 2039/0291; A61M 2205/583; A61M 2207/00
See application file for complete search history.

(56) References Cited

U.S. PATENT DOCUMENTS

| | | | |
|---|---|---|---|
| 7,988,661 B2 | 8/2011 | Silver et al. | |
| 9,248,223 B2 | 2/2016 | Van Der Kamp et al. | |
| 9,430,955 B2 | 8/2016 | Daullary | |
| 2002/0198489 A1* | 12/2002 | Silver | A61M 1/064 119/14.47 |
| 2005/0020971 A1* | 1/2005 | McKendry | A61M 1/784 604/74 |
| 2005/0059928 A1 | 3/2005 | Larsson | |
| 2005/0080351 A1 | 4/2005 | Larsson | |
| 2010/0121267 A1 | 5/2010 | Silver et al. | |
| 2011/0071466 A1 | 3/2011 | Silver et al. | |
| 2011/0301533 A1 | 12/2011 | Holshouser et al. | |
| 2012/0277728 A1 | 11/2012 | Weber et al. | |
| 2014/0031744 A1* | 1/2014 | Chen | A61M 1/066 604/74 |
| 2014/0263611 A1 | 9/2014 | Bauer | |
| 2014/0288466 A1 | 9/2014 | Alvarez et al. | |
| 2016/0058928 A1 | 3/2016 | Nowroozi et al. | |
| 2016/0206794 A1* | 7/2016 | Makower | A61M 1/064 |

FOREIGN PATENT DOCUMENTS

| | | |
|---|---|---|
| CN | 105247563 A | 1/2016 |
| CN | 105288759 A | 2/2016 |
| CN | 105555329 A | 5/2016 |
| EP | 1593402 A1 | 11/2005 |
| FR | 1067421 A | 6/1954 |
| RU | 2377023 C2 | 12/2009 |
| TW | 201121592 A | 7/2011 |
| WO | WO-2011/037841 A2 | 3/2011 |
| WO | WO-2014/063261 A1 | 5/2014 |
| WO | WO-2014/094186 A2 | 6/2014 |
| WO | WO-2014/094187 A1 | 6/2014 |
| WO | WO-2016/007561 A1 | 1/2016 |
| WO | WO-2016/145173 A1 | 9/2016 |

OTHER PUBLICATIONS

Russian Patent Application No. 2019107335/14, Office Action, dated Dec. 11, 2019.

International Search Report for Application No. PCT/EP2016/070742, dated Jun. 5, 2017.

* cited by examiner

BREAST SHIELD

CROSS-REFERENCE TO RELATED APPLICATION

The present application is the US national phase of International Application No. PCT/EP2016/070742, filed Sep. 2, 2016.

TECHNICAL FIELD

The present invention relates to a breast shield for expression of human breastmilk.

PRIOR ART

Manually operated and motor-driven breastpump units for expression of human breastmilk are known. They have a breast shield or two breast shields for sealing application to the breast. This at least one breast shield is connected to a manually operated or motor-driven breastpump directly or via a suction line. By means of the breastpump, a cyclically changing vacuum is generated which is transmitted to the breast shield in order to pump milk out of the breast.

Breastpump units are intended to allow the breastmilk to be pumped out in a manner which is as close to the natural suckling of a baby as possible. In this case, special pumping sequences having a varying negative pressure and pumping frequency are used. In addition, breast shields are provided in very different embodiments which are intended to ensure comfortable fitting on the breast thanks to soft inserts, known as liners. Also known are breast shields which are intended to stimulate the breast by massage.

Conventional breast shields have a funnel for sealing application and for receiving the breast. The funnel ends in a tubular extension which is able to be connected via an adapter both to the breastpump directly or via a suction line and to a milk collection container. In use, the nipple projects into this extension and is pulled into the extension upon application of the cyclically varying negative pressure. The extension should in this case be large enough that it does not impede the movement of the nipple.

In order that the vacuum applied can be used as optimally as possible, attempts are made to keep the volume to be evacuated as small as possible. Attempts are thus made to minimize the dead volume.

U.S. Pat. No. 4,607,596 discloses a device, the basic principle of which is intended to be able to be used in a milking apparatus for livestock and also for expression of human breastmilk. The associated breast shield has a rigid main body with a flexible insert. There are two chambers which are able to be subjected to a pulsating negative pressure, wherein the negative pressure is generated by one and the same breastpump. The first chamber is formed by the interior space in which the breast is received. The second chamber is located between the flexible insert and the main body.

In U.S. Pat. No. 7,988,661 B2, the breast shield likewise has two chambers, wherein these are able to be subjected to different pressures that are independent of one another. In particular a negative pressure and a positive pressure can be applied. That publication shows a multiplicity of different breast shields. FIGS. 16A and 16 show a breast shield with three chambers which are intended to simulate suckling by a baby. The nipple is in this case pulled lengthwise upon application of the negative pressure. The three chambers can be subjected to pressure independently of one another, such that a rotational movement about the longitudinal axis of the breast shield can also be simulated. In the embodiment according to FIG. 17, the flexible insert has inwardly directed ribs in a hollow-cylindrical region which massage and stimulate the nipple and the adjoining tissue of the breast. In the embodiments according to FIGS. 18 and 19, the chambers form indentations toward the nipple in order to thus massage the latter.

WO 2014/094186 A2 describes a breast shield unit having a flexible insert for receiving the breast and the nipple and also having a separate media separating diaphragm for protecting the vacuum source. The media separating diaphragm moves such that it does not come into contact with the nipple and thus does not impede the movement of the nipple.

WO 2014/063261 A1 discloses a breast shield having a flexible insert which simultaneously serves as a media separating diaphragm. Said flexible insert is held in a twisted manner in a hollow-cylindrical receptacle and receives the nipple. Upon application of a negative pressure between the receptacle and insert, the insert enlarges its milk aperture.

WO 2011/037841 A2 shows a breast shield which has an inflatable pad in the transition between the funnel and the tubular extension.

U.S. Pat. No. 9,248,223 B2 describes a breast shield having a soft insert which exerts a peristaltic pressure on the nipple by means of negative pressure in order to express milk.

WO 2016/007561 A1 shows a breast shield insert which is provided with grooves in the region of the nipple in order to increase the surface area.

US 2016/0058928 A1 discloses a breast shield which is intended to correspond to the mouth of a baby. The nipple is received in a flexible breast shield part which can collapse asymmetrically in order to imitate the mouth movements of the baby. The negative pressure is conducted to the breast shield via the milk collection container.

Although those relatively recent breast shields show solution attempts that are good in part in order to approach natural suckling, optimal imitation of the nature and thus the optimal shape and pressurization of a breast shield have not yet been found.

SUMMARY OF THE INVENTION

Therefore, it is an object of the invention to create an alternative method for operating a breastpump unit and also an alternative breast shield, which allow a maximum pumping performance and also a minimum pumping duration per pumping session.

This object is achieved by a method for operating a breastpump unit for expression of human breastmilk, wherein the breastpump unit has a vacuum pump for generating pressures and at least one breast shield for sealing application to a breast to be pumped. The breast shield has an inner chamber for receiving a nipple of the breast and also at least one outer chamber which at least partially surrounds the nipple. According to the invention, a first pressure is applied to the inner chamber by the vacuum pump and at least one second pressure is applied to the at least one outer chamber by the vacuum pump. An approximately temporally constant pressure is used as the first pressure and a pulsating pressure is used as the at least one second pressure. Alternatively, a pulsating pressure is used as the first pressure and an approximately temporally constant pressure is used as the at least one second pressure.

The approximately temporally constant pressure is a pressure which either remains constant over the entire period of the pumping operation or changes temporally more slowly by a multiple compared with the second pulsating pressure.

A "pulsating pressure" is understood to mean a varying pressure which varies preferably cyclically. Preferably, the pressure varies uniformly, i.e. sinusoidally. However, it can also vary nonuniformly within a cycle and/or there can be regular or irregular pauses between the cycles.

In the prior art, a pulsating, i.e. varying pressure, is applied in the breast shield cavity, in which the nipple is received, said pulsating pressure being intended to simulate the suckling action of an infant. As a result of the pressure applied, the nipple is stretched and pulled lengthwise during pumping. By contrast, the nipple is not or is scarcely stretched when the method according to the invention, referred to as first method below, is applied. Conversely, as a result of the application of the outer, varying pressure, the natural milk ducts extending in the nipple are kept open, opened regularly and/or additionally widened radially, such that the milk can flow out in an unimpeded manner.

The constant negative pressure applied in the breast shield cavity, i.e. directly at the nipple, scarcely influences the shape of the nipple and serves predominantly to maintain the position of the breast shield and to discharge the pumped out human milk.

Preferably, the values of the first pressure and of the at least one second pressure are in a range in which the nipple of the breast remains substantially unchanged in terms of length.

The first method according to the invention thus allows a maximum pumping performance. Since the diameter of the milk ducts in the nipple is maximized, a minimum pumping duration per pumping session is additionally possible.

In a preferred variant of the first method, the breast shield has a flexible inner part, known as a liner. This flexible inner part subdivides the breast shield into the inner chamber and into the at least one outer chamber. The flexible inner part is subjected to the first pressure from the inside and to the at least one second pressure from the outside.

Preferably, in order to position the breast shield on the breast, the first pressure is applied in the first chamber in a first step, in order that the flexible inner part is pulled inward into contact with the nipple, and the at least one second pressure is applied in a further step. The dead volume is minimized as a result. The nipple is massaged and the outer, varying pressure can be applied optimally to the nipple.

In an alternative variant, in order to position the breast shield on the breast, at least one third pressure is applied in the at least one second chamber in a first step, wherein the third pressure is temporally constant, wherein the flexible inner part is pulled outward by this third pressure in order to form an interior space for the purpose of receiving the nipple, wherein the first and the at least one second pressure are applied in a further step in order to express milk. As a result, the tissue of the nipple is protected optimally when it is placed inside the breast shield and the flexible inner part can subsequently fit closely on the nipple around the entire circumference.

Preferably, a negative pressure is used as the first pressure and a negative pressure and/or a positive pressure is used as the at least one second pressure. Since the second pressure is a varying negative pressure which changes at times into a positive pressure, there is a wide range of possibilities for activating and massaging the nipple.

Preferably, the first pressure and the at least one second pressure are used independently of one another. This, too, increases the range of abovementioned possibilities.

Preferably, the first pressure and the at least one second pressure are applied in dependence on one another as stipulated by a control unit.

There can be exactly one second chamber. This type of breast shield can be produced easily and cost-effectively. In another embodiment, there are at least two second chambers, which each have a second pressure applied to them independently of one another. Preferably, in this case, the ratio of the at least two second pressures relative to one another is varied over time. This allows massaging of the nipple that is as near-natural as possible during pumping, i.e. the nipple is acted upon in a similar manner to the situation in the mouth of the infant.

The abovementioned object of the invention is also achieved according to the invention by a method for operating a breastpump unit for expression of human breastmilk, wherein the breastpump unit has a vacuum pump for generating pressures and at least one breast shield for sealing application to a breast to be pumped. The breast shield has a flexible inner part having an inner chamber for receiving a nipple of the breast and at least one outer chamber which at least partially surrounds the nipple. A first pressure is applied to the inner chamber by the vacuum pump and at least one second pressure is applied to the at least one outer chamber by the vacuum pump. The flexible inner part is pressurized such that the latter fits on the nipple in an annular manner in a first position and such that it frees the nipple in the radial direction in a second position.

This method, referred to as second method below, likewise allows the breastmilk to be pumped out without the nipple being pulled lengthwise and without the diameter of the natural milk ducts decreasing. Depending on the type of pressurization, an increase in the clear width of the natural milk ducts can also be achieved.

In the prior art, the nipple is received in the breast shield in a contact-free manner. The breast shield usually fits only on the adjoining breast tissue. These breast shields massage the tissue of the breast. In the second method according to the invention, by contrast, the nipple is contacted, preferably tightly enclosed, and, depending on the variant of the second method, massaged. Preferably, only the nipple or at most a part or all of the areola is contacted.

In a preferred variant of the second method according to the invention, the first pressure pulsates and the at least one second pressure is constant. In another variant, this is reversed.

The method according to the invention, in particular the above-described first method, can be used optimally for example with breastpump units and breast shields described in the following text. The breastpump units and breast shields described in the following text can also be operated with other methods, however.

A first breastpump unit according to the invention for expression of human breastmilk has a vacuum pump for generating pressures and at least one breast shield for sealing application to a breast to be pumped. The breast shield has an inner chamber for receiving a nipple of the breast and also at least one outer chamber which at least partially surrounds the nipple. The inner chamber is configured to be subjected to a first pressure by the vacuum pump and the at least one outer chamber is configured to be subjected to at least one second pressure by the vacuum pump. In this case, the first pressure is an approximately temporally constant pressure and the at least one second pressure is a pulsating pressure.

The breast shield of this first breastpump unit preferably has a flexible inner part which subdivides the breast shield into the inner chamber and the at least one outer chamber. The flexible inner part is able to be subjected to the first pressure from the inside and to the at least one second pressure from the outside. Such flexible inner parts are often known as liners. The liner can be held releasably in a rigid or semirigid breast shield body or can be produced together therewith and not be releasable therefrom nondestructively.

This first breastpump unit preferably has at least one sensor to determine the position of the nipple during the pumping operation. This makes it possible to determine whether and optionally how much the nipple is stretched or compressed by the applied pressures. Preferably, the controller is configured to vary the first pressure and/or the at least one second pressure in accordance with this determined position of the nipple. As a result, the breastpump can be adapted individually to the requirements of the mother. As a result, it is possible for any mother to pump without her nipple being stretched too much or the milk ducts of the nipple being reduced in size too much. The at least one sensor can additionally or alternatively be used to determine the position with regard to the longitudinal axis of the breast shield at which the inner chamber collapses or the flexible inner part closes the chamber.

Various embodiments of breast shields are mentioned in the following text, which can be used in particular in the abovementioned methods and in the breastpump units described in this text. These breast shields each have an application region for sealing application to the human breast and an inner chamber for receiving a nipple of the breast.

A first of these breast shields according to the invention has at least one outer chamber which at least partially surrounds the nipple. The inner chamber is configured to be subjected to a first pressure by the vacuum pump and the at least one outer chamber is configured to be subjected to at least one second pressure by the vacuum pump. The first pressure is an approximately temporally constant pressure and the at least one second pressure is a pulsating pressure.

Since the breast shield only has to enclose the nipple, it can be configured in a relatively small manner. It can also be used in a concealed and discreet manner under clothing in a hands-free solution. In addition, the dead volume is minimized and so the breastpump unit generating the two pressures can also be configured in a correspondingly small manner. This minimizes the costs and optimizes the performance.

This first breast shield preferably has a flexible inner part which subdivides the breast shield into the inner chamber and the at least one outer chamber. The flexible inner part is able to be subjected to the first pressure from the inside and to the at least one second pressure from the outside. Preferably, the flexible inner part is a flexible insert which is connected fixedly or releasably to a breast shield body. The flexible inner part simplifies the production of the breast shield. In addition, it allows sealing application to the nipple and comfortable and effective massage and optimal stimulation of the nipple.

In a second of these breast shields according to the invention, the inner chamber is configured in a conical manner over the entire receiving region. The conical configuration prevents the nipple from being pulled too greatly lengthwise by the applied negative pressure and thus prevents the diameter of the natural milk ducts from being reduced. In addition, the conical shape allows optimal fitted enclosure of the nipple along the entire length of the nipple.

The inner chamber of this second breast shield has an inner wall which, in addition to the conical shape or as an alternative to this conical shape, is equipped with retaining means for retaining the nipple during the pumping operation. These retaining means prevent the nipple from being pulled lengthwise during pumping.

A third of these breast shields according to the invention is provided with at least one sensor for determining the position of the nipple during the pumping operation. As already mentioned above, the pressures can be set in accordance with this measured signal such that the change in length of the nipple is optimized. In particular, the change is minimized.

The inner chamber of a fourth of these breast shields according to the invention has a longitudinal axis. The inner chamber collapses in accordance with an applied pressure. The breast shield is provided with at least one sensor for determining the position at which the inner chamber collapses. This collapsing likewise holds back the nipple and thus prevents undesired stretching thereof. Thanks to the sensor, it is possible to determine whether the inner chamber collapses at the desired point. If not, the applied pressure or applied pressures can be varied and/or the position of the breast shield on the nipple can be corrected.

The application region of a fifth of the breast shields according to the invention ends in an encircling, soft and sealing pad on the breast side. The pad preferably has an encircling inflatable cavity. This pad allows pressure-free and yet sealed fitting on the nipple or the areola. This is comfortable for the mother in the event of sensitive or already inflamed breasts. In addition, the breast shield does not create any kink on the breast even if the breast shield is pressed on too strongly by the mother. The flow of milk is not impaired or influenced.

A sixth of the breast shields according to the invention has an encircling receiving pocket on the breast side for collecting breastmilk drops when the breast shield is removed. Thus, when the breast shield is removed from the breast, no drops can be lost. All of the breastmilk to the very last drop can be used. This is important in particular for premature infants when the mother can initially scarcely produce milk herself.

Preferably, this sixth breast shield has a flexible inner part which forms the application region for sealing application to the human breast and an inner chamber for receiving a nipple of the breast, wherein the encircling pocket is formed in the flexible inner part. Preferably, the flexible inner part is able to be everted such that the collected milk drops can be removed more easily from the breast shield.

A seventh of the breast shields according to the invention has an outer breast shield body and a flexible inner part, wherein the flexible inner part forms the application region for sealing application to the human breast. The flexible inner part subdivides the breast shield into the inner chamber for receiving a nipple of the breast and into at least one outer chamber which at least partially surrounds the nipple. The inner chamber is configured to be subjected to a first pressure by the vacuum pump and the at least one outer chamber is configured to be subjected to at least one second pressure by the vacuum pump. The flexible inner part is configured in one piece. The breast shield has a further chamber in the form of a cavity which is subdivided by the at least one outer chamber in that a fixed or releasable connection between the flexible inner part and the outer breast shield body forms an encircling partition wall. The cavity is arranged in the application region of the breast shield. As a result, an inflatable pad can be created in order to position the breast shield optimally on the nipple. The same subdivision principle can also be used to create more than one outer chamber which can be subjected to different pressures in order in this way to massage and stimulate the nipple differently at different points.

An eighth of the breast shields according to the invention defines a longitudinal axis. The inner chamber is bounded by an outer region which is formed in an asymmetrical manner. At least one subregion of the outer region has an outer chamber, the inner side of which is able to be subjected to a pressure. Preferably, a subregion of the outer region has a variable rigidity and/or hardness, for example by way of a rigid setting element. This breast shield imitates the mouth of an infant with palate and tongue.

A second breast shield unit according to the invention of a breastpump unit for expression of human breastmilk has a vacuum pump for generating pressures. The breast shield unit comprises a breast shield having an interior space for receiving a nipple and a flexible milk collection container. The interior space has a first opening for receiving the nipple and, as the only other opening, a connecting opening to the milk collection container, wherein the breast shield is connected to the milk collection container in an airtight manner via this opening. Means are provided which cyclically enlarge the interior space for the purpose of generating a negative pressure in the interior space for expression of the breastmilk. This second breast shield unit can be a development of the above-described first breast shield unit. This breast shield unit minimizes the contact of the milk with the ambient air, and so contamination of the milk can be largely avoided. This is important in particular in the field of neonatology.

The means of this second breast shield unit are preferably flexible tongues and lines that actuate the flexible tongues. Such a breast shield unit can be produced cost-effectively and easily. It is also relatively easy to use. It can in turn be used optimally in the field of neonatology.

A ninth of the breast shields according to the invention has a fan which blows air in the direction of the breast. This air blown onto the breast imitates the breathing of the baby and thus promotes the production of milk by the mother.

The features of all of the abovementioned breast shields can optionally be combined with one another in order to create further breast shields within the meaning of the invention.

Further embodiments are specified in the dependent claims.

BRIEF DESCRIPTION OF THE DRAWINGS

Preferred embodiments of the invention are described in the following text with reference to the drawings, which serve merely for illustration and should not be interpreted in a limiting manner. In the drawings:

FIG. 8e shows a cross section through the breast shield according to FIG. 8a;

FIG. 8f shows a perspective schematic illustration of a setting element of the breast shield according to FIG. 8a;

FIG. 10b shows a perspective schematic illustration of a part of the breast shield according to FIG. 10a;

FIG. 12b shows a variant of the breast shield according to FIG. 12a.

Identical or similar elements are provided with the same reference signs.

DESCRIPTION OF PREFERRED EMBODIMENTS

Figure 1:
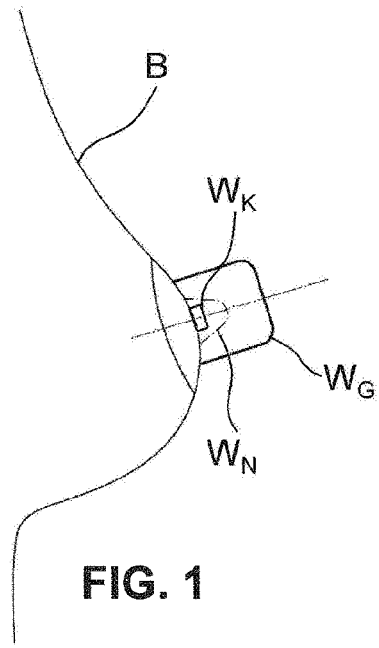
FIG. 1 shows a schematic illustration of a human breast with possible shapes of the nipple.

FIG. 1 shows a schematic illustration of a human breast B with a nipple $W_N$ of average size, a small nipple $W_K$ and a large nipple $W_G$. The diameter of the nipples of different mothers lies in a range from about 10 mm to about 24 mm, with an average value of about 16 mm. The length of the nipple without external influence varies from mother to mother from about 3 mm to about 20 mm, with an average value of about 7 mm.

The breast shields in the prior art did not normally contact the nipples, and so the variance in the nipples of different mothers could remain disregarded. However, the breast shields according to the invention are preferably fitted on the nipples and are intended to stimulate the latter by fitting closely on and radially releasing them in order to extract milk. Preferably, the breast shields even fit only on the nipple or only additionally on the areola, but not on the surrounding breast tissue of the breast. The breast shields described in the following text can preferably be used for the entire abovementioned range of possible nipples, either in that they are themselves offered in a corresponding manner in different sizes or, more preferably, in that they adapt to the shape and size of the particular nipple by way of their shape and, if present, their flexible inner part.

Figure 2A:
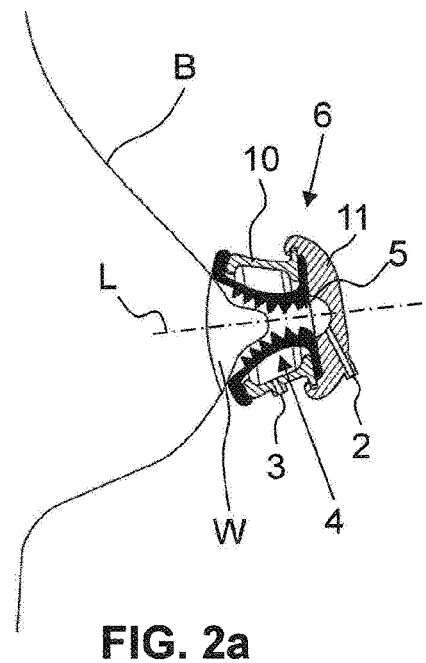
FIG. 2a shows a schematic illustration of a breast shield according to the invention in a first embodiment before a pressure is applied.
Figure 2B:
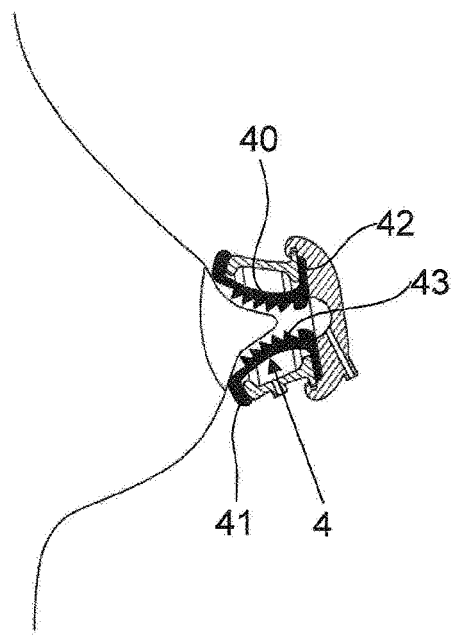
FIG. 2b shows the breast shield according to FIG. 2a with pressure, for example vacuum, applied in an inner chamber.
Figure 2C:
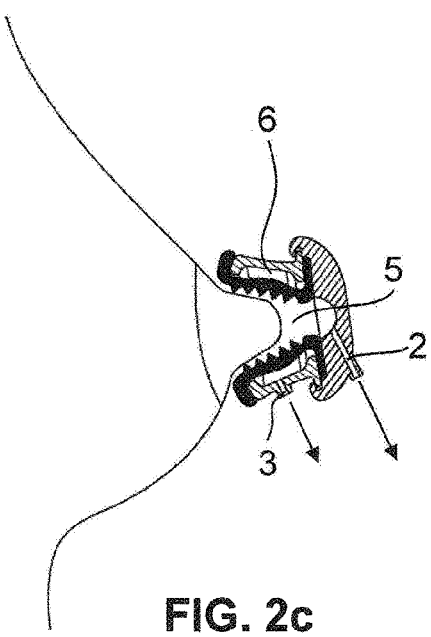
FIG. 2c shows the breast shield according to FIG. 2a with pressures applied in the inner chamber and in an outer chamber.

FIGS. 2a to 2c illustrate a first embodiment of a breast shield according to the invention. It has a rigid or semirigid breast shield body 1 which is produced preferably from plastics material. In this example, the breast shield body 1 is designed in two parts. It has a base 10 and a cover 11.

Figure 13:
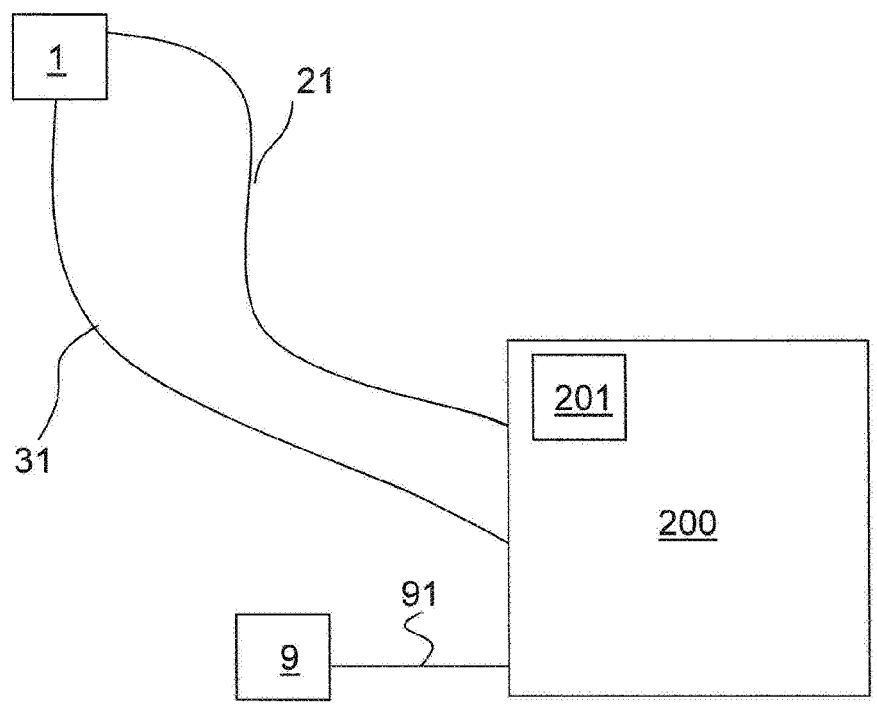
FIG. 13 shows a schematic illustration of a breastpump unit according to the invention.

The cover 11 has a first vacuum connection 2 for connecting to a vacuum pump. The vacuum pump has at least one vacuum unit for generating a negative pressure. The vacuum pump is illustrated in FIG. 13 and is described later on in this text.

The base 10 is formed in a substantially frustoconical manner in this example. It can also have some other shape; for example, it can be configured in a hollow-cylindrical manner. In this example, it has a breast-side fastening flange and a pump-side fastening flange. Provided on the base 10 is a second vacuum connection 3 which allows a connection to preferably one and the same pumping unit or to another pumping unit of the vacuum pump.

The base 10 and the cover 11 enclose a cavity which is subdivided into an inner chamber 5 and an outer chamber 6 by a flexible inner part 4, also known as a liner.

The inner chamber 5 has a breast-side opening through which the nipple W is introduced into the breast shield during use. On the pump side, the first vacuum connection 2 ends in the inner chamber 5 and thus connects the latter to the vacuum pump. The inner chamber 5 preferably has only these two openings. In other embodiments, the inner chamber 5 also has a milk connection.

The outer chamber 6 is preferably formed in a completely closed manner apart from the second vacuum connection 3. The walls of the outer chamber 6 are preferably formed by the rigid or semirigid breast shield body 1 and the flexible insert element 4.

The flexible inner part 4 is fitted over the base 10 and is held in this position thereby. It can also be molded on. Preferably, it consists of a soft plastics material, preferably of silicone. If it is a loose part, it is preferably held in a clamped manner by means of the cover 11.

The flexible inner part 4 has a main body 40, an encircling application region 41 and an encircling fastening flange 42. The fastening flange 42 is clamped between the cover 11 and base 10. By way of the application region 41, the breast shield is applied to or fitted on the nipple W and/or the areola surrounding the latter in a sealing manner, when it is used as intended. The application region 41 is in this example the underside of the thickened flange which is fitted over the base 10. As a result, although it is soft on the breast side, it is stabilized on its rear side by the base 10, such that the mother can exert sufficient pressure force for fitting in a sealing manner by hand or by way of a hands-free bra. The thickened region is configured for example as an encircling hollow or solid pad.

The main body 40 can move relative to the longitudinal center axis L of the breast shield between these two flanges, as is apparent from viewing FIGS. 2a, 2b and 2c together.

The main body 40 can be embodied in a smooth-walled manner. In this embodiment, it has retaining elements 43 for the nipple W. The nipple W can also not stretch too much when negative pressure is applied in the inner chamber 5, since its extent is limited by the retaining elements 43.

Preferably, the retaining elements 43 are formed by encircling ribs which extend along at least a part of the length of the main body. The ribs preferably face toward the breast side. However, they can also project radially inward toward the longitudinal center axis L of the breast shield. Preferably, the ribs narrow toward their free end. However, they can also have some other shape, for example have rounded free ends. The ribs are preferably configured in a relatively soft manner in order not to irritate or even to injure the nipple W. However, they are preferably rigid enough to prevent excess lengthening of the nipple W during the expression of the milk. Instead of ribs, it is also possible to use other types of retaining elements 43, for example by suitably choosing a material of an inherently smooth inner wall of the main body 40, i.e. by choosing a material with a sufficiently large coefficient of friction.

In the situation according to FIG. 2a, the breast shield has been placed on the nipple W and surrounds the latter in a sealing manner. A vacuum has not yet been applied. The main body 40 of the flexible inner part 4 is at a distance from the nipple W or is in slight contact therewith, without exerting a substantial pressure thereon. The nipple W has its natural shape, uninfluenced by external forces.

In the situation according to FIG. 2b, a temporally approximately constant negative pressure has been applied via the first vacuum connection 2 by means of the vacuum pump. It can remain constant throughout the subsequent pumping operation or be adapted as stipulated by the mother or a controller of the vacuum pump, but be constant again for a subsequent period until the next adaptation. However, it can also change cyclically, wherein the cycle time is very long, for example one or more minutes. Alternatively or in addition, the mean value of the cycle can also vary.

As can be readily seen in FIG. 2b, the main body 40 of the flexible inner part 4 is pulled inward toward the longitudinal center axis L on account of the negative pressure prevailing in the inner chamber 5. The nipple W is contacted and firmly enclosed. The retaining means 43 prevent the nipple W from being pulled excessively lengthwise at the same time, however. Preferably, the possible lengthening of the nipple W is only a few percent, for example less than 20%.

In the situation according to FIG. 2c, the constant negative pressure has continued to be maintained in the inner chamber 5. Via the second vacuum connection 3, a pulsating negative pressure has simultaneously been applied in the outer chamber 6, it being possible for said pulsating negative pressure to additionally have a positive pressure component. Preferably, the applied negative pressure moves between a maximum negative pressure and atmospheric pressure, however, or even exhibits a continuously present basic vacuum. The second maximum negative pressure is preferably greater than the first maximum negative pressure in terms of absolute value, i.e. the outer chamber 6 is evacuated more than the inner chamber 5.

As a result of the application of the pulsating negative pressure in the outer chamber 6, the main body 40 of the flexible inner part 4 is pulled outward again and away from the longitudinal center axis L of the breast shield. The main body can relax again and bulges outward again. This massaging effect has the result that the nipple W relaxes again and the natural milk ducts of the nipple W widen.

Milk flows out of the nipple W into the inner chamber 5 in this third situation. Depending on the embodiment of the breast shield, there can be a further connection which is connected to a milk collection container directly or via a line. In this embodiment, the milk flows through the first vacuum connection 2 to the breastpump and from there into the milk collection container. In other words, the vacuum line for the constant negative pressure serves simultaneously as a milk line.

As a result of the application of the constant pressure in the inner chamber 5 and the pulsating pressure in the outer chamber 6, the method according to the invention can be carried out, said method relaxing the nipple W and preferably pulling it outward and as a result opening the natural milk ducts. However, this breast shield can also be used in other methods, for example in that the inner chamber 5 is subjected to a pulsating, i.e. cyclically changing negative pressure and the outer chamber 6 is subjected to a pulsating and/or a constant pressure, depending on the variant. This results in a massaging effect. The same also goes for the breast shields described in the following text.

Figure 3A:
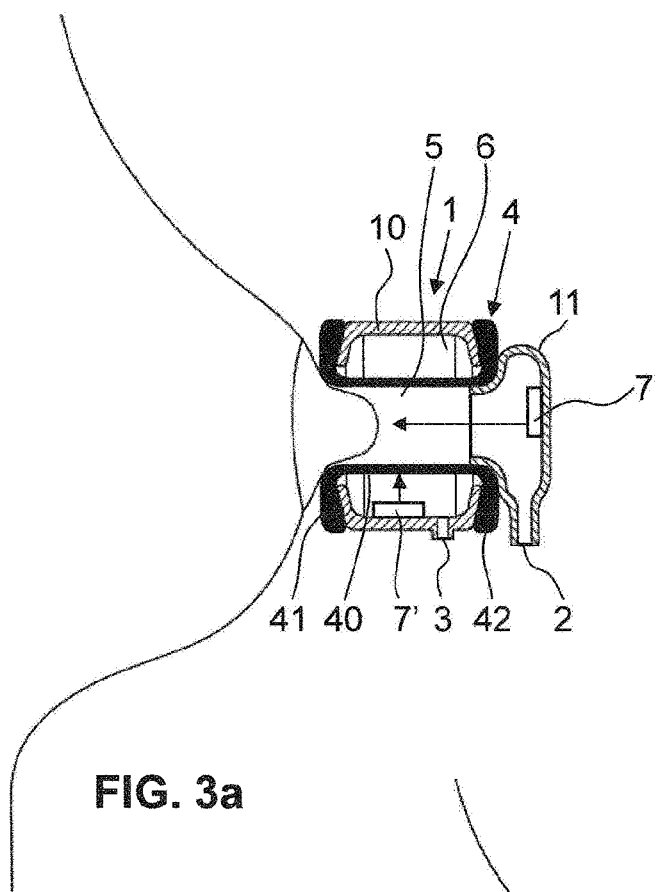
FIG. 3a shows a schematic illustration of a breast shield according to the invention in a second embodiment with sensors, in a starting position.
Figure 3B:
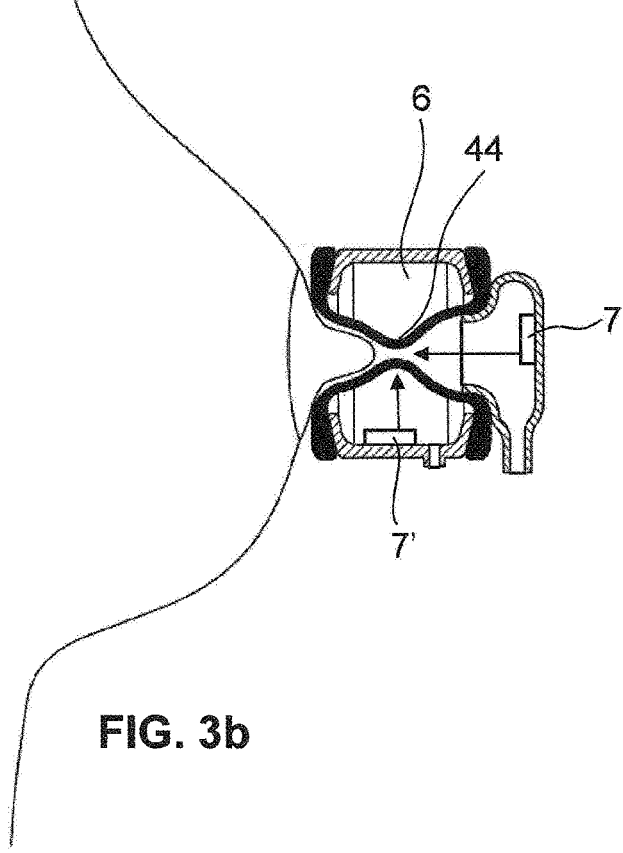
FIG. 3b shows the breast shield according to FIG. 3a with pressure applied in an inner chamber.

FIGS. 3a and 3b illustrate a second embodiment of a breast shield according to the invention. The basic structure of the breast shield is the same as in the first exemplary embodiment and therefore will not be explained in more detail here. The rigid or semirigid breast shield body 1, in which the flexible inner part 4 is arranged, is once again present. The first vacuum connection leads into the inner chamber 5 and the second vacuum connection 3 leads into the outer chamber 6. The outer chamber 6 encircles the outer side of the flexible inner part 4. The inner wall of the main body 40 is configured in a smooth manner in this illustration. In other variants, it is likewise provided with retaining elements 43, for example with ribs. A constant negative pressure is again preferably applied in the inner chamber 5 and a pulsating negative pressure that exceeds the latter in terms of magnitude is present in the outer chamber 6. In other words, here too, the method according to the invention can be applied, in which the lengthening of the nipple W is limited and the nipple W is massaged by means of the flexible inner part 4 and optionally radially stretched as a result of the negative pressure in the outer chamber 6.

FIG. 3a shows the situation in which no negative pressure has been applied or a negative pressure has been applied in both chambers 5, 6. FIG. 3b shows the situation when a negative pressure has been applied only in the inner chamber 5 or said negative pressure predominates at least in terms of magnitude.

It is clear from FIG. 3b how the main body 40 has been pulled inward toward the longitudinal center axis L of the breast shield, wherein the main body 40 partially or entirely closes the passage formed between the breast-side end of the breast shield and the pump-side end of the breast shield. In FIG. 3b, it is not yet completely closed. The closure 44 preferably takes place immediately in front of the free end of the nipple W, such that the latter is prevented from extending further in the longitudinal direction by the closure 44. The closure 44 thus forms a retaining means for the nipple W.

In this embodiment, too, the inner side of the main body 40 can be provided either with a smooth surface or with additional retaining means.

This embodiment preferably has at least one, preferably two sensors 7, 7'. The first sensor 7 is arranged in line with the nipple W, in this case in the cover 11, and measures along the longitudinal center axis L of the breast shield. It detects the position of the tip of the nipple W and of the closure 44. The second sensor 7' is arranged radially with respect to the main body 40 of the flexible inner part 4 and detects the radial movement of the main body 40. Both sensors 7, 7' are preferably optical sensors. Instead of a single second sensor 7', it is also possible for a plurality of sensors 7' that are arranged in a manner distributed around the circumference of the breast shield to be used.

With the aid of these two sensors 7, 7', the position of the closure 40 and the change of the nipple W can be determined. These sensors 7, 7' are preferably connected to an optical and/or acoustic display and/or to a controller of the breastpump. In accordance with these measurement signals, the pumping parameters, for example the pumping frequency and/or the vacuum level can be altered such that the closure 44 comes to rest at an optimal point for the particular size of the nipple W and thus can optimally limit the stretching of the nipple W in the longitudinal direction.

FIGS. 4a to 4d illustrate a third embodiment of the breast shield according to the invention. The breast shield body 1 is configured here in one piece and again has the two connections 2 and 3 and the inner chamber 5 and the outer chamber 6. The flexible inner part 4 has been fitted over the two end faces of the breast shield body 1 and held in this way. The main body 40 of the flexible inner part is configured in a substantially hollow-cylindrical manner, wherein it transitions at its breast-side end into an outwardly directed, encircling and self-contained arch 400. This arch 400 can have the same wall thickness as the cylindrical part of the main body 40. However, it can also be embodied in a thickened manner. The main body 40 can have been produced in a multicomponent injection-molding process, in particular in a two-component injection-molding process.

The encircling breast-side flange of the flexible inner part 4 is directed outward and in turn forms the encircling, self-contained application region 41 for application to the nipple W or the adjoining areola. The application region 41 is preferably embodied in a thickened manner. Preferably, it is relatively soft, in a similar manner to an encircling pad.

The inner chamber 5 is again subjected to a constant vacuum, and a pulsating, in particular cyclically changing vacuum is applied to the outer chamber 6.

Figure 4A:
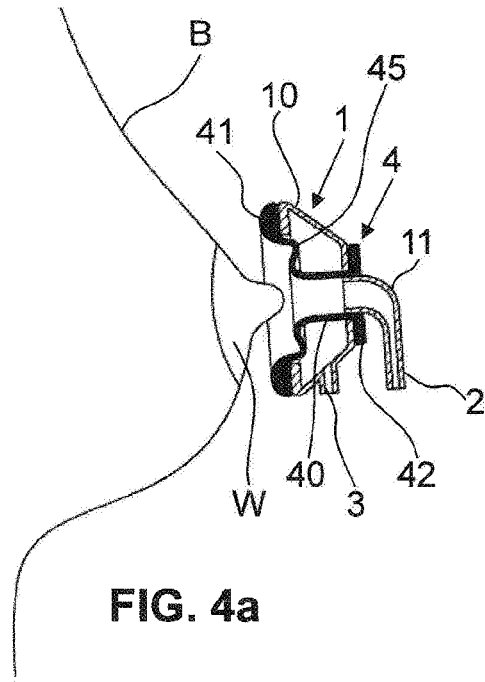
FIG. 4a shows a schematic illustration of a breast shield according to the invention in a fourth embodiment before it is fitted on the breast.
Figure 4B:
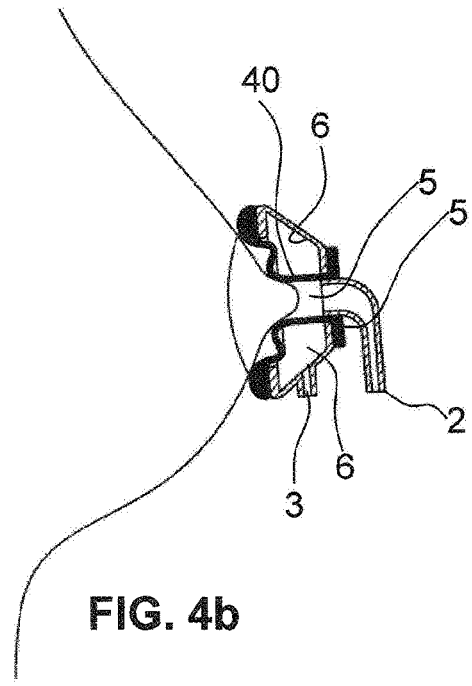
FIG. 4b shows the breast shield according to FIG. 4a while it is being fitted on the breast.

In FIG. 4a, the breast shield is illustrated in the basic state before it is placed on the breast. In FIG. 4b, the breast shield has been positioned on the nipple W and encloses the latter. In this case, the free end of the nipple W is received in the hollow-cylindrical part of the main body 40. This part can also have some other shape. For example, it can be frusto-conical.

Figure 4C:
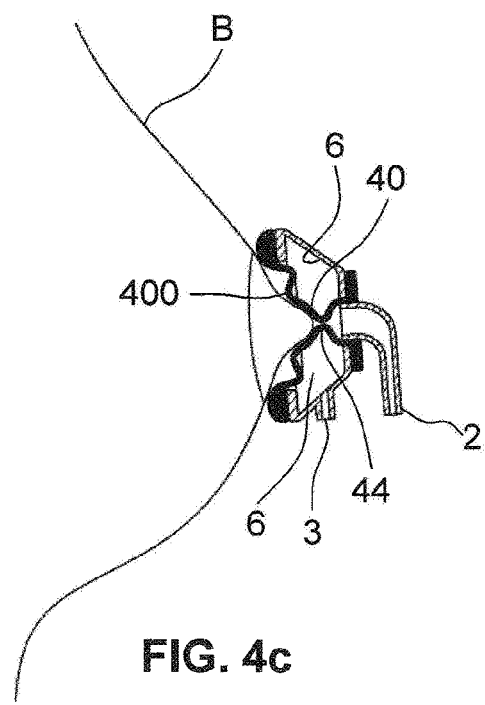
FIG. 4c shows the breast shield according to FIG. 4a with pressure applied in an inner chamber.
Figure 4D:
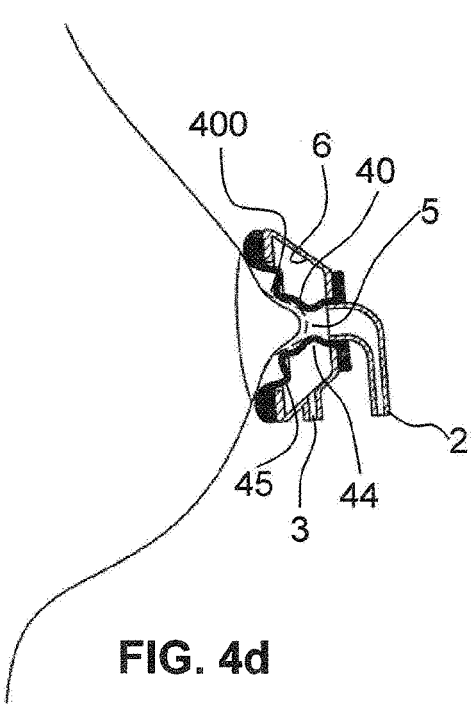
FIG. 4d shows the breast shield according to FIG. 4a with pressures applied in the inner chamber and in an outer chamber.

In FIG. 4c, the inner chamber 5 is subjected to the constant pressure. The main body 40 of the flexible inner part is pulled toward the longitudinal center axis L of the breast shield, the arch 400 changes its shape and the main body 40 again forms a closure 44. As a result, the nipple W is again prevented from extending longitudinally without it being exposed to excessive external forces. If the pulsating vacuum is now applied to the interior space of the outer chamber 6, the main body 40 moves at least partially back outward radially and at least partially frees the nipple W again. In this case, the arch 400 changes its shape, but preferably fits on the nipple W throughout the pumping operation and surrounds the latter. Preferably, the arch 400 is configured in such a soft and flexible manner that it does not produce any pressure points on the nipple W. As a result, the flow of milk is not impeded.

The movement of the arch 400 on the nipple 4 and/or on the areola results in the nipple W being massaged and stimulated and thus in increased milk output. The continuous fitting of the arch 400 can be ensured for example in that the magnitude of the applied constant vacuum is higher than the magnitude of the pulsating vacuum throughout the cycle.

Figure 5A:
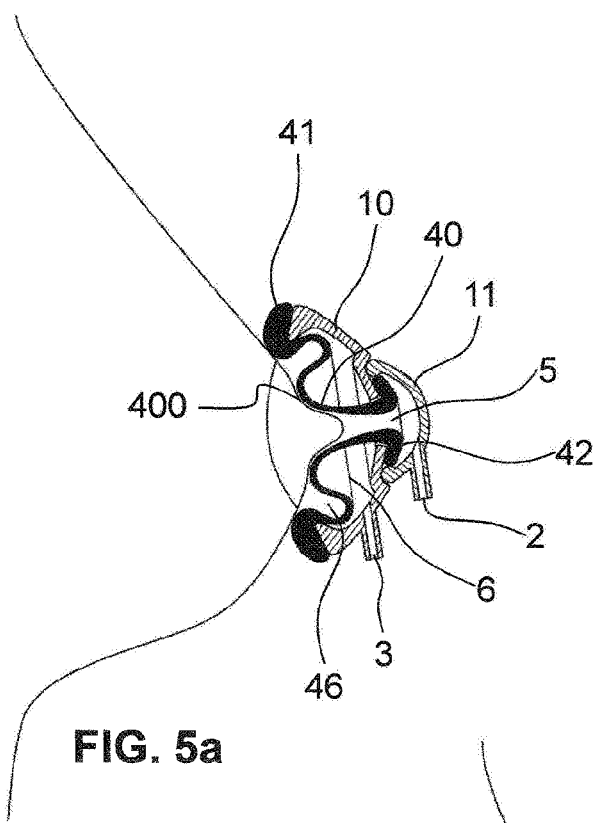
FIG. 5a shows a schematic illustration of a breast shield according to the invention in a fourth embodiment while it is being fitted on the breast.
Figure 5B:
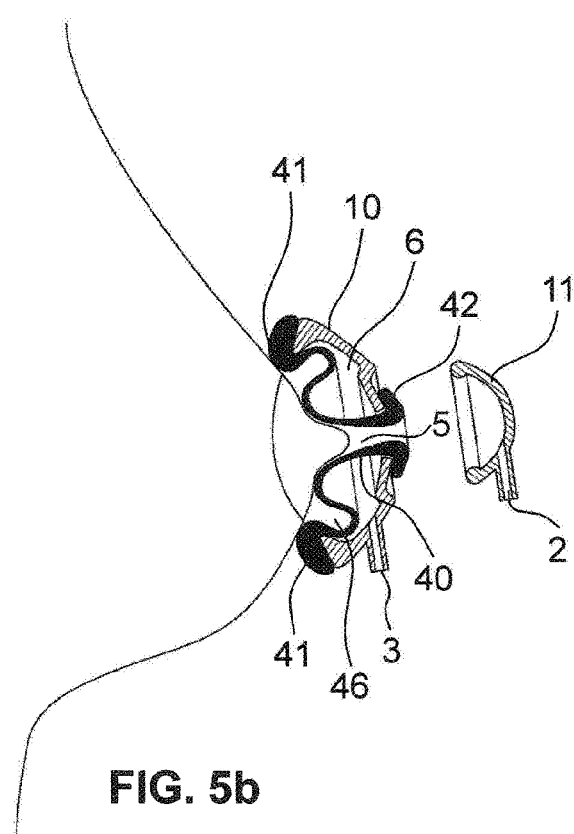
FIG. 5b shows the breast shield according to FIG. 5a with the cover removed.

The embodiment according to FIGS. 5a and 5b is optimally usable in particular for mothers with very low milk production, in particular mothers of premature infants. Here too, the parts already explained above are not described again in detail. The applied pressures are preferably as described above. In addition to the arch 400 that preferably fits continuously on the nipple W, a pocket 46 for receiving individual milk drops is provided. The pocket 46 is preferably configured so as to encircle the breast shield such that it does not have any influence on the rotational position of the breast shield on the nipple W. Pumped-out milk which is not suctioned through the milk duct, or, depending on the embodiment, through the first vacuum connection 2, is collected in this pocket 46. When the breast shield is removed after the nipple W has been pumped, this additional milk is retained in the pocket 46 and can likewise be collected and used. In this way, no drop of the precious breastmilk is lost.

FIGS. 6a to 6d show a further embodiment of the breast shield according to the invention, which is preferably operated with a constant internal pressure and a pulsating external pressure.

In this embodiment, the flexible inner part 4 is fitted at its pump-side end over a connection piece 12 which forms the first vacuum connection 2. The main body 40 transitions here on the breast side into an arch which forms a contacting region 45. This contacting region 45 contacts the nipple W preferably throughout the pumping operation, wherein the contacting region 45 preferably fits on the nipple W around the entire circumference of the latter as in the previous example.

Figure 6A:
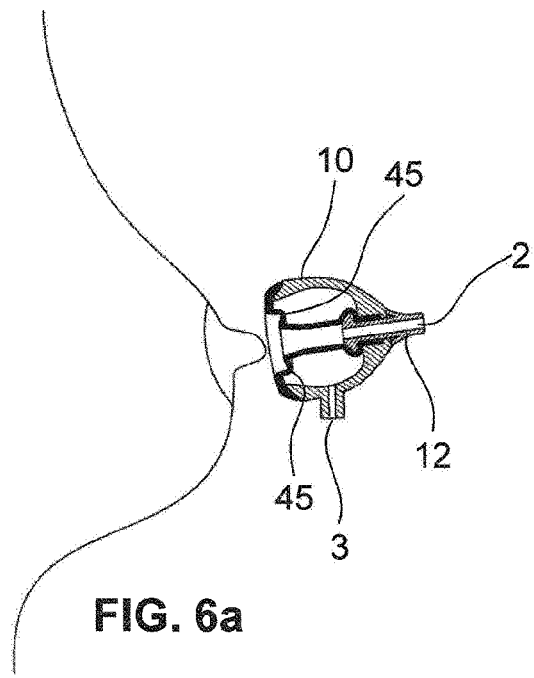
FIG. 6a shows a schematic illustration of a breast shield according to the invention in a fifth embodiment before it is fitted on the breast.

In FIG. 6a, the breast shield is illustrated in the basic state. The inside diameter of the main body 40 is preferably the same as or less than the diameter of a smallest nipple W or of a nipple W in question.

Figure 6B:
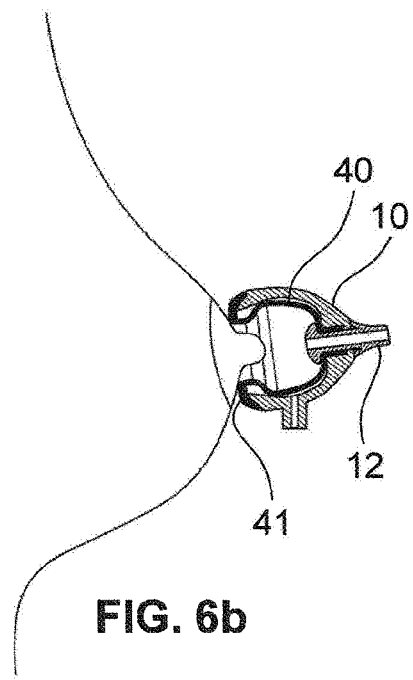
FIG. 6b shows the breast shield according to FIG. 6a in the fully opened state after it has been fitted on the breast.

In FIG. 6b, the breast shield has been placed on the nipple W, wherein a constant negative pressure has been applied in the outer chamber 6 but not in the inner chamber 5. As a result, the main body 40 of the flexible inner part 4 has moved radially outward. The inner chamber 5, which serves to receive the nipple W, has reached its maximum volume. As a result, the breast shield can be fitted easily over the nipple W. This is advantageous in particular in the case of sensitive or inflamed nipples W.

Figure 6C:
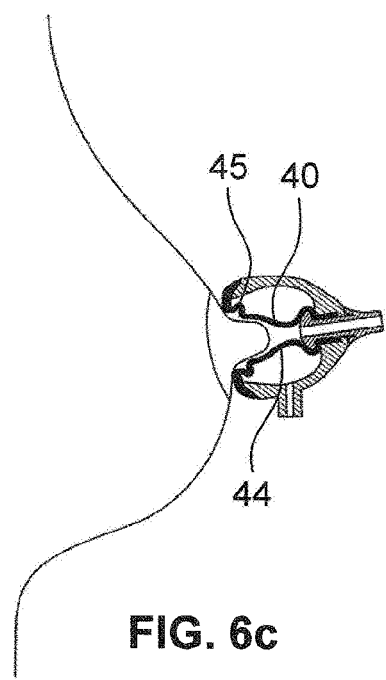
FIG. 6c shows the breast shield according to FIG. 6a in the closed state after it has been fitted on the breast.

Subsequently, as illustrated in FIG. 6c, a negative pressure is generated in the inner chamber 5 and preferably the absolute value of the negative pressure in the outer chamber 6 is reduced, set to atmospheric pressure or even raised to a positive pressure. As a result, the main body 40 is pulled toward the longitudinal center axis L of the breast shield and toward the nipple W. The application region 45 encloses the nipple W and fits on the latter around the entire circumference. In the end region of the nipple W, the closure 44 is again formed. The effective pumping operation can now begin.

Figure 6D:
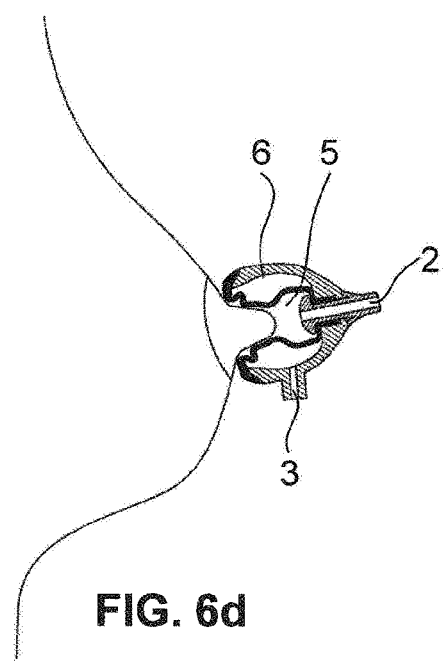
FIG. 6d shows the breast shield according to FIG. 6a during the expression of breastmilk.

This is illustrated in FIG. 6d. Via the first connection 2, a constant vacuum has been applied to the inner chamber 5, and via the connection 3, a pulsating, preferably higher vacuum in terms of magnitude has been applied.

During the pumping operation, the shape of the flexible inner part 4 changes from the shape according to FIG. 6d to the shape according to FIG. 6c and back. Pumping takes place in FIG. 6d and massaging and stimulation take place in FIG. 6c.

The breast shield can be removed easily and painlessly once the pumping operation has been completed, when the situation according to FIG. 6b is brought about again by means of the applied pressures.

This embodiment has the further advantage that the flexible inner part 4 does not have any wrinkles or creases and that the flexible inner part 4 can be brought to the optimal fit with regard to the individual nipple W merely by a change in pressure upon application of the breast shield to the breast.

The embodiment according to FIGS. 7a to 7d differs from the above essentially in that, in addition to the outer chamber 6, a further encircling outer closed cavity 410 is formed, which can also be subjected to pressure. Accordingly, two second connections 3, 30 are provided. This is achieved, in this embodiment, in that the flexible inner part 4 has a circumferential partition wall 47 which subdivides the region between the rigid or semirigid breast shield body 1 and the flexible inner part 4 into two regions. Preferably, this partition wall 47 is configured such that it is connected or is connectable around its entire circumference to a correspondingly protruding or recessed counterpart on the inner wall of the breast shield body 1.

The outer chamber 6 remote from the breast is again used to move the main body 40 of the flexible inner part 4, analogously to the examples already described above. The inflatable cavity 410 close to the breast forms an encircling inflatable pad for the application region 41.

Figure 7A:
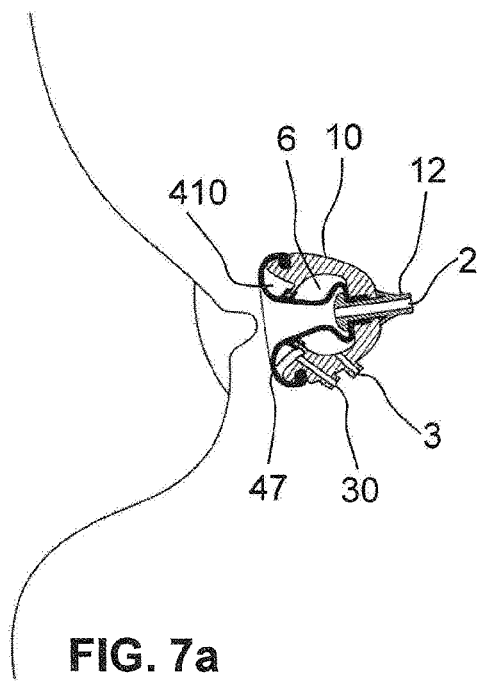
FIG. 7a shows a schematic illustration of a breast shield according to the invention in a sixth embodiment before it is fitted on the breast.

In FIG. 7a, the breast shield is illustrated in the basic state. The inside diameter of the breast receiving region of the flexible inner part 4 is preferably the same as or greater than the diameter of a nipple W.

Figure 7B:
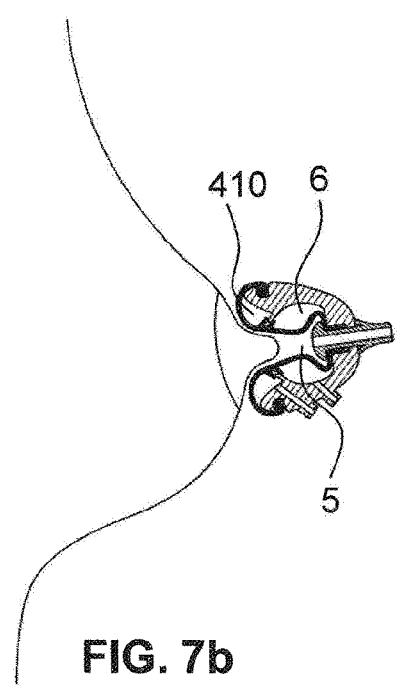
FIG. 7b shows the breast shield according to FIG. 7a while it is being fitted on the breast.
Figure 7C:
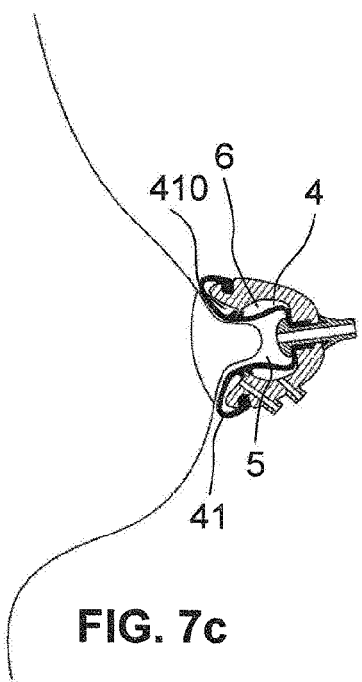
FIG. 7c shows the breast shield according to FIG. 7a after it has been fitted on the breast.

In FIG. 7b, it has been applied to the nipple W. A constant positive pressure is applied to the cavity 410 close to the breast via the second connection 30, in order that the cavity 410 expands and a pumped-up encircling pad is formed which fits on the nipple W and/or on the areola. The nipple W is in this case received in the flexible inner part 4, wherein it is slightly compressed According to FIG. 7b, the positive pressure in the pad, i.e. in the cavity 410 is now reduced. Preferably, atmospheric pressure or a negative pressure is generated in this cavity 410. As a result, the nipple W can relax again and shorten in terms of length. However, it continues to be held in the flexible inner part 4 such that the latter contacts the nipple W around its entire circumference.

Figure 7D:
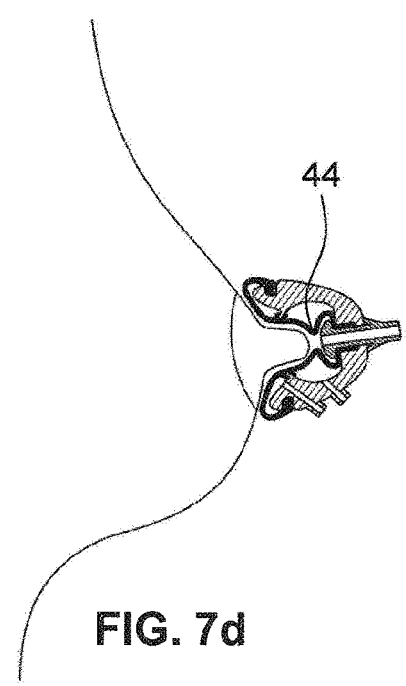
FIG. 7d shows the breast shield according to FIG. 7a during the expression of breastmilk.

The pumping operation, which is illustrated in FIG. 7d, subsequently begins. A constant negative pressure is generated in the inner chamber 5 via the first vacuum connection 2. A pulsating negative pressure is generated in the outer chamber 6 close to the pump and thus remote from the breast via the second vacuum connection 3. This in turn results in massaging and stimulation of the nipple W and in milk output.

FIGS. 8a to 8f illustrate a further embodiment of a breast shield according to the invention. This simulates the conditions in the mouth of an infant.

The rigid or semirigid breast shield body is again provided with the reference sign 1. Again, it has a first vacuum connection 2 for applying a constant pressure, in particular a vacuum, in an inner chamber 5. A second vacuum connection 3 for applying a pulsating negative pressure leads to an outer chamber 6. The nipple W is received in the inner chamber 5 as in the above-described exemplary embodiments.

Arranged in the breast shield body 1 is a flexible inner part 8, which is now no longer formed in one piece, as in the previous examples. Instead, it has an upper part 80, 81, 82, which imitates the palate of the infant, and a lower part 84, which imitates the tongue of the infant and thus forms a tongue part. Both parts 80, 81, 82, 84 are preferably connected firmly to the breast shield body 1, wherein they are movable relative to the latter in order to vary the size of the inner and outer chambers 5, 6. The lower part 84 bounds the outer chamber 6 together with an adjacent region of the breast shield body 1. The upper part 80, 81, 82 bounds the inner chamber 5 together with an adjacent region of the breast shield body 1 and with the lower part 84.

The upper part has an end face 82 directed toward the breast, said face serving as an application region for sealing application to the nipple W or the areola. The lower part 84 has a corresponding counterpart which, as an application region, bears the reference numeral 41.

The upper region 80, 81, 82 can consist of regions with different hardnesses in that the materials are chosen in an appropriate manner. It can be formed in one or more pieces. In this example, it is formed in two pieces, wherein the application region 82 close to the breast and the first region 81 adjoining the latter are configured to be harder than the second region 80 remote from the breast. The second region 80 forms the rear palate part and the first region 81 forms the front palate part. The rear palate part 80 is accordingly formed in a downwardly curved manner and, depending on position, bounds or closes the inner chamber 5 toward the first vacuum connection 2. The front and the rear palate part 81, 80 adjoin one another and are connected to one another.

Figure 8A:
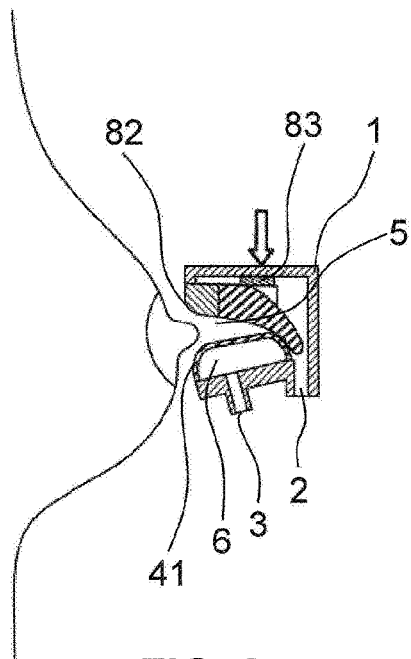
FIG. 8a shows a schematic illustration of a breast shield according to the invention in a seventh embodiment before it is fitted on the breast.

In the upper region between the breast shield body 1 and the two palate parts 80, 81, a setting element 83 is held so as to be slidable in the longitudinal direction of the breast shield. By means of this setting element 83, the hardness of the palate can be varied in that its position is varied with respect to the two palate parts 80, 81. In FIG. 8a, it is located in the region remote from the breast exclusively over the softer rear palate part 80 and has an influence on the behavior of the breast shield during the pumping operation. In the other figures, the setting part 83 has been pushed closer to the breast and also covers a part of the front palate part 81. The covered region is thus stiffened and its movement restricted. The behavior of the flexible inner part 8 during the pumping operation is influenced. The arrows directed vertically downward in FIGS. 8a to 8e show the position of the setting element 83.

Figure 8B:
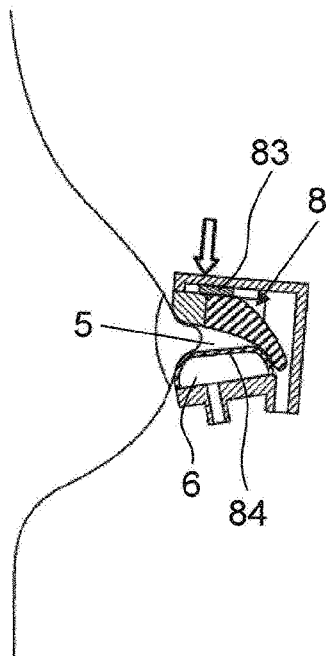
FIG. 8b shows the breast shield according to FIG. 8a while it is being fitted on the breast.
Figure 8C:
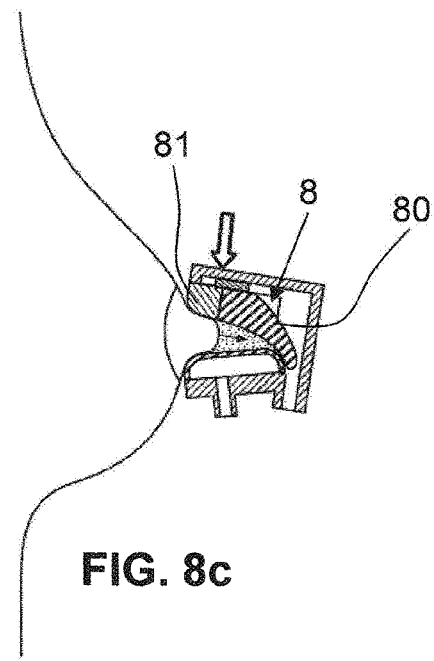
FIG. 8c shows the breast shield according to FIG. 8a during the expression of breastmilk in a first situation.
Figure 8D:
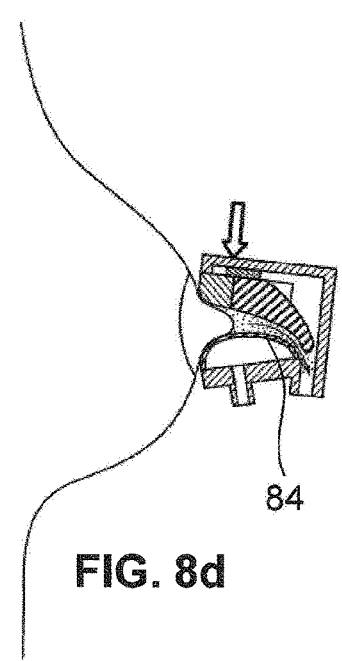
FIG. 8d shows the breast shield according to FIG. 8a during the expression of breastmilk in a second situation.
Figure 8E:
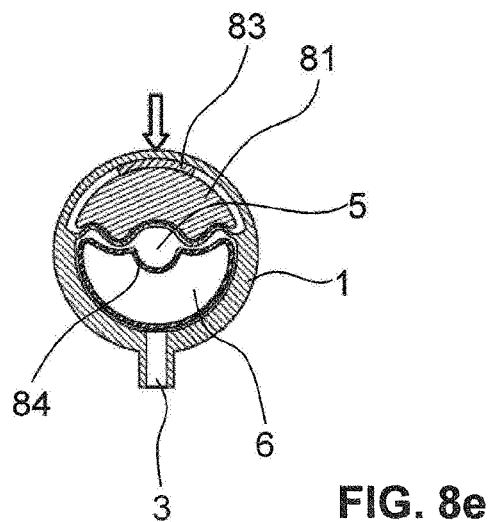
Figure 8F:
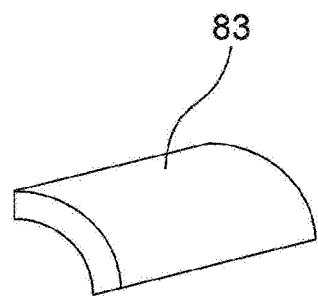

FIG. 8f illustrates a possible embodiment of such a setting element 83. It is a portion of a rigid hollow cylinder. Other shapes are possible. Furthermore, rather than being slid, the setting part 83 can also be moved into the corresponding position by other types of movement. Instead of a mechanical setting element 83, the palate parts can also be formed in a hollow manner and their rigidity can be varied by application of a positive pressure.

In FIG. 8a, the breast shield is illustrated again in the basic state when not in use. In FIG. 8b, the breast shield is fitted over the nipple W such that the nipple W is received between the two palate parts 80, 81 and the tongue part 84.

According to FIG. 8c, a constant negative pressure is subsequently applied to the inner chamber 5 and a pulsating negative pressure is applied under the tongue part 84, i.e. in the outer chamber 6.

The nipple W is massaged and stimulated in a similar manner to in a mouth of an infant, wherein, here too, although longitudinal extension of the nipple W with respect to the second vacuum connection 2 does take place, it is limited. This limiting takes place substantially as a result of the downwardly curved shape of the rear palate part 80. The milk flowing out of the nipple W is indicated by dots in the figures and illustrated by an arrow. This embodiment can, like those that have already been described, be combined with one or more of the above-described sensors 7, 7' for detecting the nipple W and the closure.

Figure 9:
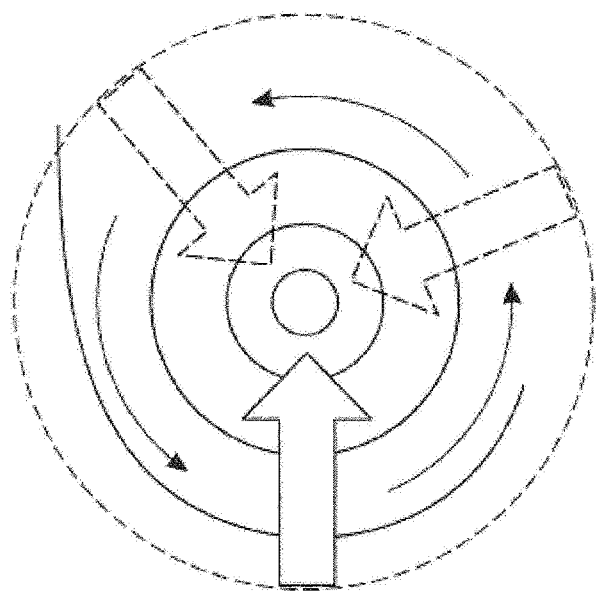
FIG. 9 shows a schematic illustration of the forces that act on a nipple during pumping as seen from the front in the direction of the breast.

FIG. 9 illustrates a variant of pressure application. In this case, a breast shield is provided in which the negative pressure is applied in the outer chamber 6 such that it rotates temporally through 360°. In the situation according to FIG. 9, the pressure of the flexible inner part 4 is currently acting on the nipple W from below. This is demonstrated by the straight arrow illustrated with solid lines. The dashed arrows show that the pressure acting on the nipple W rotates about the longitudinal center axis L of the breast shield and that rotating massage and stimulation of the nipple W thus take place. This can be achieved easily by a corresponding configuration, e.g. by subdivision of the outer chamber 6.

FIGS. 10a to 10e illustrate a breastpump unit according to the invention. As can clearly be seen in FIG. 10a, it has a rigid main body 1', a flexible breast shield 4' and a milk collection container 9. The breast shield 4' and the milk collection container 9 are formed in one piece with one another and jointly form a flexible element. The flexible element is produced from a soft material, for example from silicone. The wall thickness of the flexible element is relatively thin; preferably, it is similar to a membrane or film.

The flexible element forms a bag having an opening, the shape of which is suitable for fitting in a sealing manner on the breast without forming creases. Preferably, the opening is round, elliptical or oval. The edge of the opening is preferably reinforced, for example with a cord insert or by a thickened configuration. This reinforced edge forms the application region 41 of the breast shield 4', which fits on the breast in a sealing manner during use. The front region of the bag that is close to the breast thus forms the breast shield 4' having the flexible main body 40 and the application region 41. The rear region that is remote from the breast forms the milk collection container 9. At least one pocket 49 and preferably a plurality of pockets 49 are formed in the central region of the flexible element. A rigid or elastic ring 90 is preferably provided, which encloses the ends of the pockets 49 that are remote from the breast.

Figure 10A:
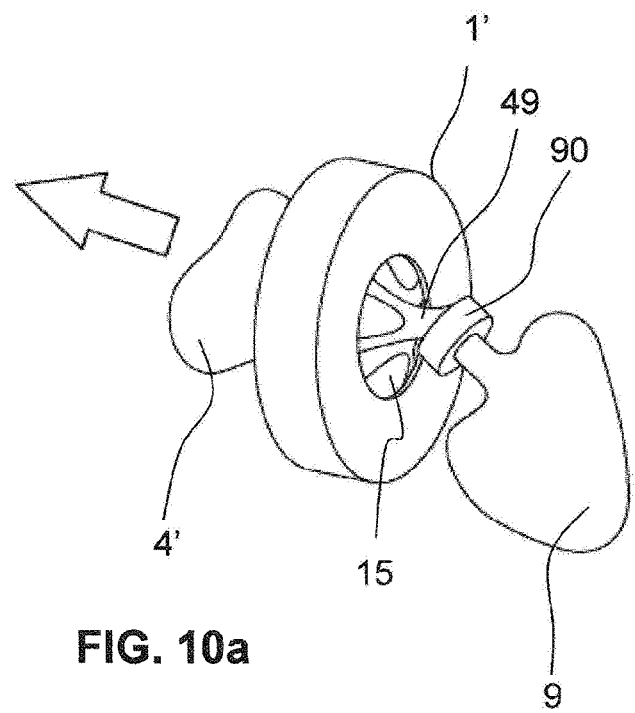
FIG. 10a shows a perspective schematic illustration of a breastpump unit according to the invention having a breast shield and milk collection container in an eighth embodiment.
Figure 10B:
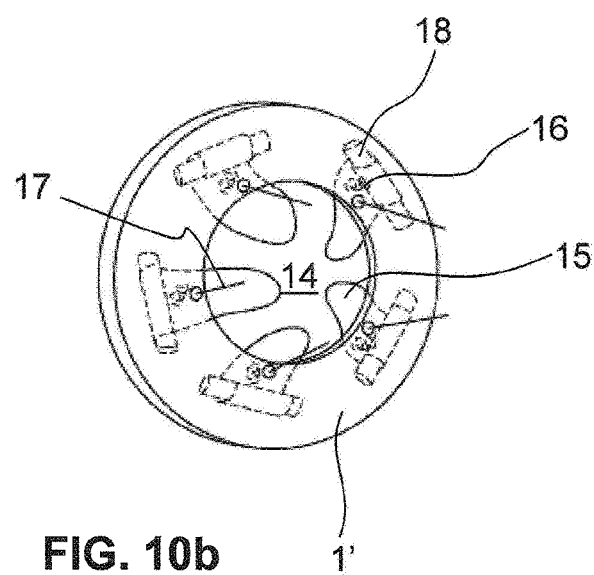

The main body 1' is readily discernible in FIG. 10a. It is formed in an annular manner and has a central passage opening 14. Distributed around this central passage opening 14 are a plurality of flexible tongues 15 in the form of leaf springs, the free ends of which are directed toward the central passage opening 14 and which pass through the central passage opening 14. The flexible tongues 15 are fastened to the main body 1' by pins 18. In the region close to the pins, the spring tongues 15 are supported on the wall inner side, remote from the breast, of the main body 1' by means of coil springs 16. This is clearly discernible in FIG. 10e. Also fastened to each flexible tongue 15 is a line 17 or cord which is likewise guided through the central passage opening 14 or, as illustrated here, through a separate opening 14' (see FIG. 10d). An individual separate opening 14' can be provided for each line 17. These lines 17 and separate openings 14' are not illustrated in FIG. 10a.

Figure 10C:
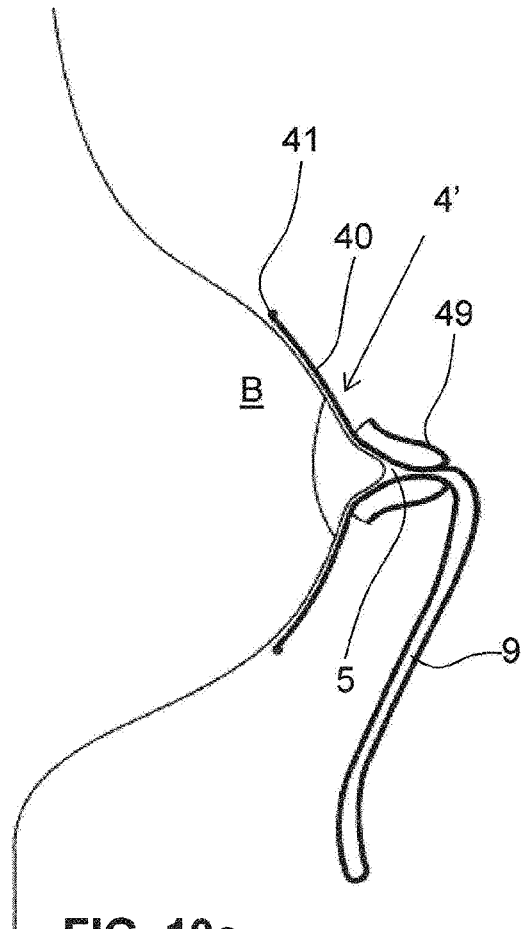
FIG. 10c shows a schematic cross section through the breast shield having a milk collection container according to FIG. 10a before use.
Figure 10D:
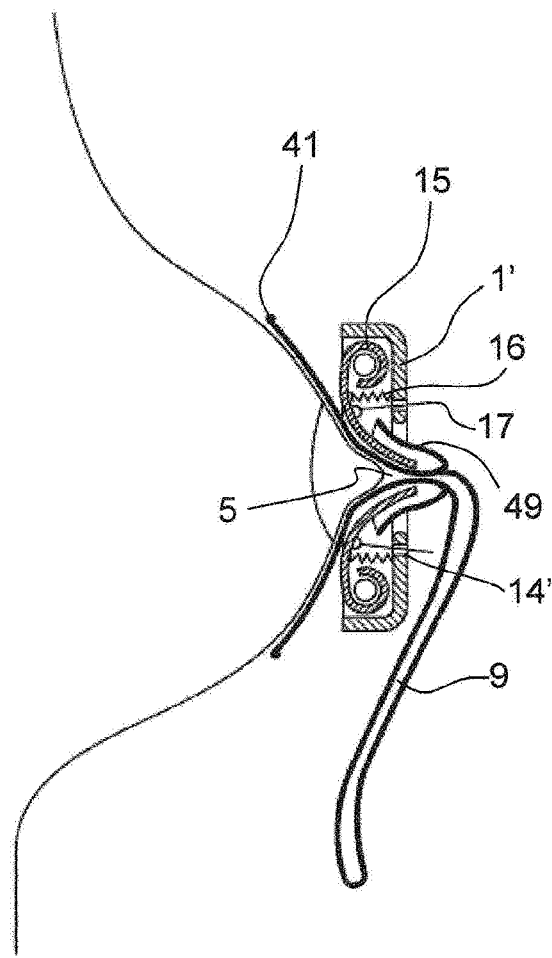
FIG. 10d shows a schematic cross section through the breastpump unit according to FIG. 10a before use.
Figure 10E:
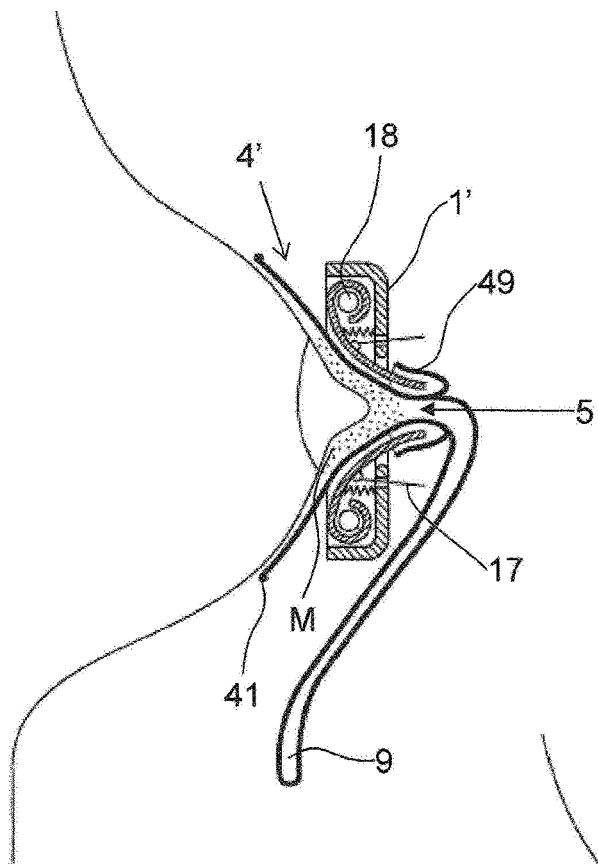
FIG. 10e shows the breastpump unit according to FIG. 10d during pumping in a first position.
Figure 10F:
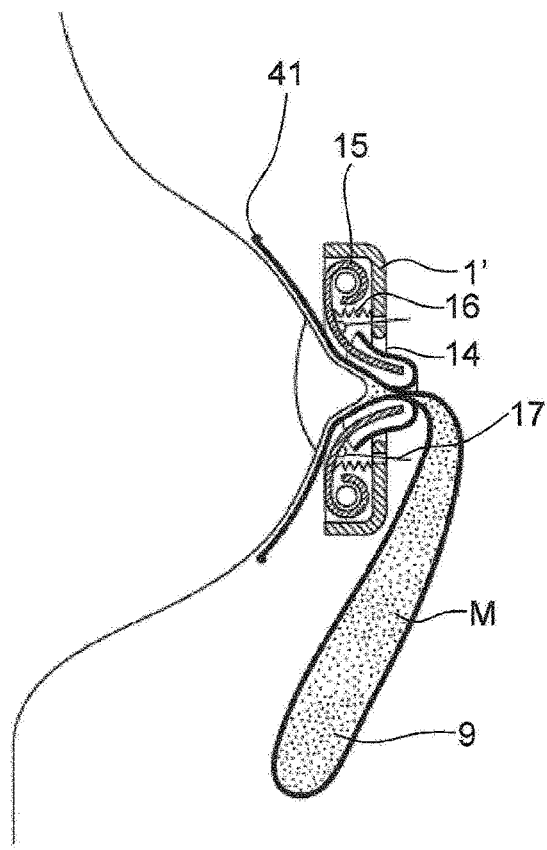
FIG. 10f shows the breastpump unit according to FIG. 10d during pumping in a second position.

The coil springs 16 can be arranged between the lines 17 and the pins 18, as is illustrated in FIGS. 10d to 10f. However, it is also possible to arrange the lines 17 between the pins 18 and the coil springs 16, as is the case in FIG. 10g.

The assembly of this breastpump unit according to the invention and its mode of operation can be explained readily with reference to FIGS. 10c to 10f. In FIG. 10c, the one-piece flexible element is illustrated, which forms the breast shield 4' with the milk collection bag 9. In practice, it is not used or applied to the breast as such on its own. However, the figure makes it easier to understand the invention. The breast shield preferably surrounds not only the nipple W but also the surrounding breast tissue B. It is preferably applied to the breast tissue B in a sealing manner. The flexible element is in this case applied to the nipple W such that the pockets 49 are located in the region of the nipple. Preferably, they project beyond the end of the nipple W.

In FIG. 10d, the entire breast shield unit, as is placed on the nipple W in practice, is now discernible. The flexible element passes through the main body 1', wherein the flexible tongues 15 are pushed into the pockets 49 of the flexible element and are held therein. The lines 17 are illustrated in a shortened manner. They usually end together in a tensioning device (not illustrated here) which is preferably manually operable. The tensioning device is for example a knob or rod to which all of the lines 17 are fastened and which can be held in the hand. It can alternatively be configured for example in the form of a slider, part of a housing which is likewise not illustrated here.

In the position according to FIG. 10d, the nipple W is enclosed and slightly compressed by the flexible tongues 15. Since the flexible tongues 15 are inclined toward one another toward the free end of the nipple W, the longitudinal extension of the nipple W is limited. In this initial state before the milk is pumped out, the milk collection container 9 is compressed. There is no air in the milk collection container 9. The region in front of the nipple W, formed by the flexible tongues 15, is the inner chamber 5.

In FIG. 10e, the pumping operation has begun. By pulling on the lines 17, the flexible tongues 15 can be raised counter to the force of the coil springs 16. The nipple W is freed at its circumference and can extend and relax. Milk flows out of the nipple W into the inner chamber 5 as a result. The milk is illustrated by dots in the figures and provided with the reference sign M. By reducing the tension on the lines 17, the flexible tongues 15 are lowered again and massage the nipple W. As a result, the extracted milk M is additionally pushed into the milk collection container 9. By repeated tensing and releasing of the lines 17, i.e. by repeated raising and lowering of the flexible tongues 15, the nipple W is massaged and stimulated. Upon releasing, the natural milk ducts widen, and milk can be extracted optimally and without an external source of suction.

Figure 10G:
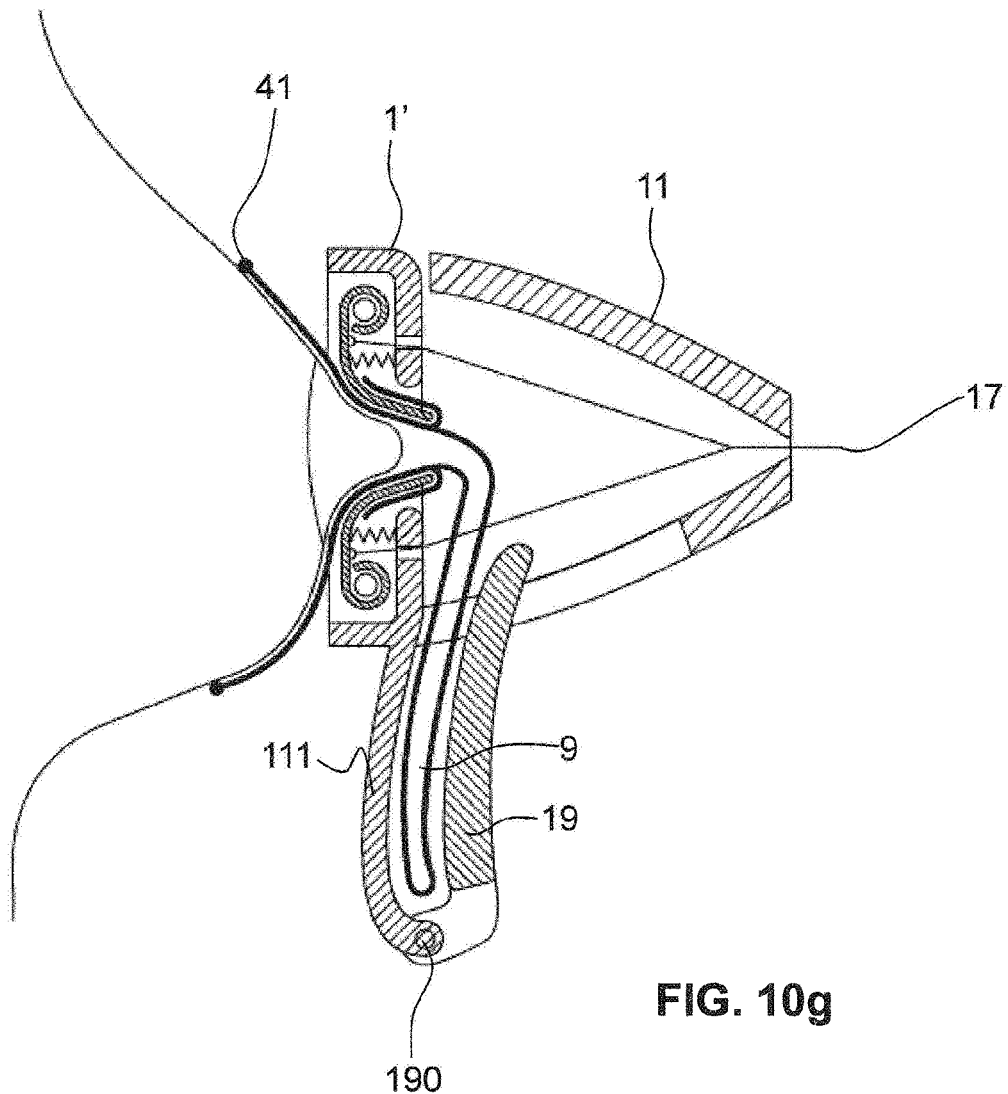
FIG. 10g shows a variant of the breastpump unit according to FIG. 10d.

The milk collection container 9 can already be supplied as an airvoid flexible tube by the manufacturer. FIG. 10g illustrates a possibility as to how it is possible to ensure, prior to use, that the milk collection container 9 is airvoid. The main body is provided with a cover 11 which, for the one part, receives the lines 17. For the other part, a pressing lever 19 is movable therein. The pressing lever 19 is connected to an extension 111 of the main body 1' via a hinge 190. The extension 111 and the pressing lever 19 together form a receptacle for the milk collection container 9. If the pressing lever 19 is now pressed in the direction of the extension 111, the milk collection container 9 is compressed and any residual air remaining therein is pressed out via the breast shield 4'. During the extraction of the breastmilk, the pressing lever 19 is subsequently freed again.

Figure 11:
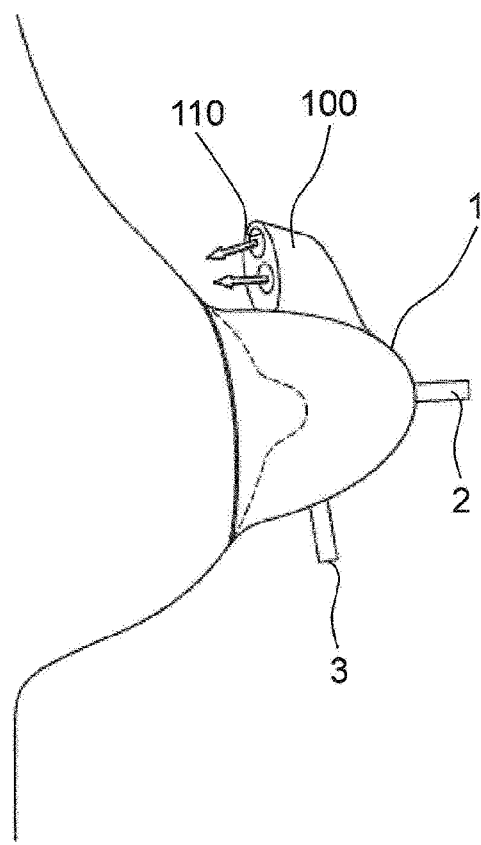
FIG. 11 shows a perspective schematic illustration of a breast shield according to the invention having a milk collection container in a ninth embodiment.

FIG. 11 illustrates a further embodiment of the breast shield according to the invention. One of the above-described breast shields or a breast shield of known type can be used for this. The breast shield body 1 is illustrated only schematically here. It can have some other shape and size. In particular, it can also receive a larger region of the breast tissue, like the known conventional breast shields.

According to the invention, the breast shield is provided with air outlet openings 110 through which air flows actively in the direction of the breast. In other words, the breast is blown on through the breast shield. An exhaust of the breastpump unit can be used for example as a corresponding fan or the fan can be a blower or ventilator which is arranged on or in the breast shield body. Other types are possible to form the fan in order to generate an airstream.

In FIG. 11, purely schematically, an attachment 100 has been placed on the breast shield body 1, wherein the attachment 100 has the air outlet openings 110 for blowing air on the breast. Preferably, the air outlet openings are located only in a subregion of the circumference of the breast shield, in order to simulate a nose of the infant.

Figure 12A:
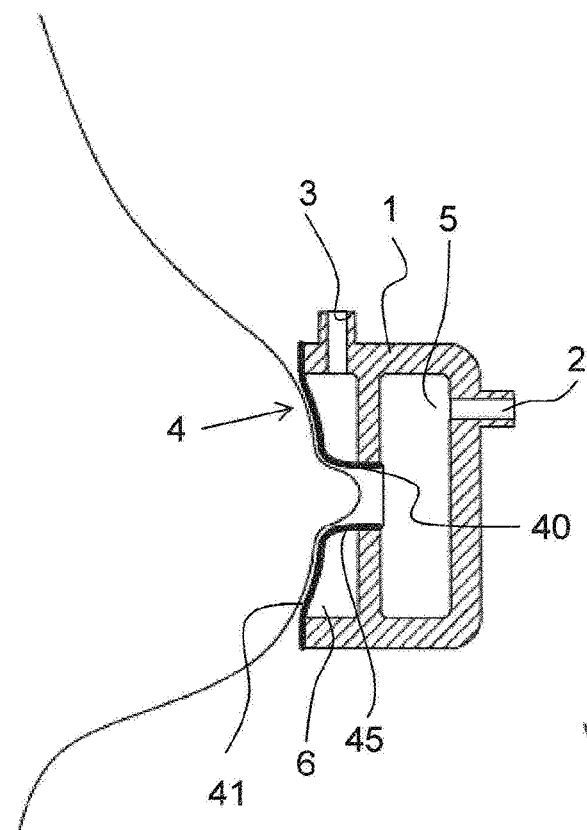
FIG. 12a shows a schematic illustration of a breast shield according to the invention having a milk collection container in a tenth embodiment.
Figure 12B:
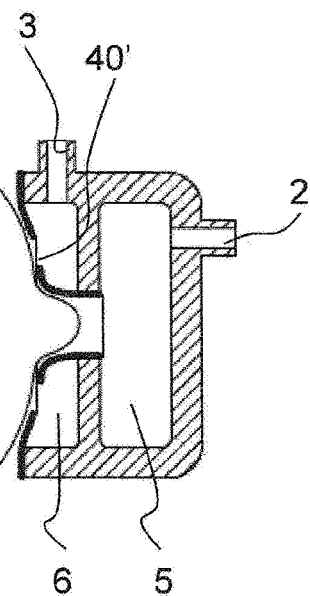

FIGS. 12a and 12b illustrate a further embodiment of the breast shield according to the invention in two variants. It again has a breast shield body 1 and a flexible inner part 4 having an application region 41. The breast shield again surrounds at most the nipple W and the areola. The nipple W is enclosed tightly by the main body 40 of the flexible inner part 4.

In the embodiment according to FIG. 12a, a temporally constant or approximately constant vacuum is applied via the first vacuum connection 2 in the inner chamber 5 into which the milk flows. Via the second vacuum connection 3, a pulsating vacuum is applied in the outer chamber 6, which surrounds the nipple W. The nipple W is massaged and the natural milk ducts open and close during the pumping operation.

In the embodiment according to FIG. 12b, a pulsating vacuum is applied via the first vacuum connection 2 and a temporally constant or approximately constant vacuum is applied via the second vacuum connection 3. In this way, the natural milk ducts are kept open throughout the pumping operation, since the nipple W is pulled radially outward on account of the negative pressure in the outer chamber 6. The main body 40 of the inner part 4 has one or more interruptions 40' in the embodiment according to FIG. 12b.

In both embodiments according to FIGS. 12a and 12b, the nipple W is enclosed annularly by the main body 40 of the flexible inner part, which firmly encloses the nipple W like a mouth of an infant.

FIG. 13 schematically illustrates a breastpump unit as can be used with the abovementioned breast shields, apart from the embodiment according to FIGS. 10a to 10g. It has the breast shield, in this case having the breast shield body 1. The first vacuum connection 2 of the breast shield body 1 is connected to a vacuum pump 200 by a first vacuum line 21. The vacuum pump 200 can have one or more pumping units and a control unit 201. If sensors are provided in the breast shield, the sensor unit receives the data from the sensors and accordingly controls the at least one pumping unit.

The second vacuum connection 3 is likewise connected to the vacuum pump 200 via a second vacuum line 31. A milk line 91 leads from the vacuum pump to the milk collection container 9. As set out above, in all the breast shields described, apart from the embodiment according to FIGS. 10a to 10g, a separate milk connection can lead from the inner chamber 5 to a milk collection container either directly or via a line. However, it is also possible, as illustrated here, to use the first vacuum connection 2 as the milk connection and to conduct the milk through the first vacuum line to the breastpump or to an upstream chamber and from there into the milk collection container 9 directly or via a milk line 91. Alternative paths for the extracted milk are also possible.

The inventive concepts are not limited to the above-described embodiments. These should be considered to be purely schematic in order to understand the basic principles of the invention. These basic principles can also be realized with other mechanical means. Most of the breast shields presented here fit closely on the nipple around the entire circumference and, on account of the selected pressurization, are collapsible at a well-defined point in an actively controlled manner. As a result, the nipple is prevented from extending in the longitudinal direction. By contrast, radial extension of the nipple is promoted. The stimulation of the nipple takes place in practice in a mechanical manner by frictional and shear forces in all of the breast shields illustrated here. The milk ducts are kept open for as long as possible. The breast shields themselves can be configured in a relatively small manner, such that they are also usable as hand-free solutions. In addition, they do not irritate the breast, since they only enclose the nipple and at most also the areola.

The method according to the invention, the breastpump units according to the invention and the breast shields according to the invention allow a maximum pumping performance and a minimum pumping duration per pumping session.

| LIST OF REFERENCE SIGNS | |
|---|---|
| 1 | Breast shield body |
| 1' | Main body |
| 10 | Base |
| 100 | Attachment |
| 110 | Air outlet openings |
| 111 | Extension |
| 11 | Cover |
| 12 | Connection piece |
| 14 | Passage opening |
| 14' | Separate opening |
| 15 | Flexible tongue |
| 16 | Coil spring |
| 17 | Line |
| 18 | Pin |
| 19 | Pressing lever |
| 190 | Hinge |
| 2 | First vacuum connection |
| 21 | First vacuum line |
| 200 | Vacuum pump |
| 201 | Control unit |
| 3 | Second vacuum connection |
| 30 | Third vacuum connection |
| 31 | Second vacuum line |
| 4 | Flexible inner part |
| 4' | Breast shield |
| 40 | Main body |
| 40' | Interruption |
| 400 | Arch |
| 41 | Application region |
| 410 | Cavity |
| 42 | Fastening flange |
| 43 | Retaining element |
| 44 | Closure |
| 440 | Arch |
| 45 | Contacting region |
| 46 | Pocket |
| 47 | Partition wall |
| 49 | Receiving pocket |
| 5 | Inner chamber |
| 6 | Outer chamber |
| 7 | First sensor |
| 7' | Second sensor |
| 8 | Flexible inner part |
| 80 | Rear palate part |
| 81 | Front palate part |
| 82 | Application region |
| 83 | Setting element |
| 84 | Tongue part |
| 9 | Milk collection container |
| 90 | Ring |
| 91 | Milk line |
| B | Breast |
| M | Milk |
| W | Nipple |
| $W_N$ | Average nipple |
| $W_K$ | Small nipple |
| $W_G$ | Large nipple |
| L | Longitudinal center axis |

The invention claimed is:

1. A method for operating a breastpump unit for expression of human breastmilk, wherein the breastpump unit has a vacuum pump for generating pressures and at least one breast shield for sealing application to a breast to be pumped, wherein the breast shield has an inner chamber for receiving a nipple (W) of the breast and also at least one outer chamber for partially surrounding the nipple (W), wherein a first pressure is applied to the inner chamber by the vacuum pump and at least one second pressure is applied to the at least one outer chamber by the vacuum pump, wherein a) a substantially constant pressure is used throughout a pumping session as the first pressure and a pulsating pressure is used as the at least one second pressure, or wherein b) a pulsating pressure is used as the first pressure and a substantially constant pressure is used throughout the pumping session as the at least one second pressure, and wherein at least one sensor determines the position of the nipple during the pumping operation,
wherein a controller varies the first pressure and the at least one second pressure in accordance with the position of the nipple determined by the at least one sensor.

2. The method as claimed in claim 1, wherein the breast shield has a flexible inner part which subdivides the breast shield into the inner chamber and the at least one outer chamber, and wherein the flexible inner part is subjected to the first pressure from the inside and to the at least one second pressure from the outside.

3. The method as claimed in claim 2, wherein, in order to position the breast shield on the breast, the first pressure is applied in the inner chamber in a first step, in order that the flexible inner part is pulled inward into contact with the nipple (W), and wherein the at least one second pressure is applied in a further step.

4. The method as claimed in claim 2, wherein, in order to position the breast shield on the breast, at least one third pressure is applied in the at least one outer chamber in a first step, wherein the third pressure is substantially constant throughout the pumping session, wherein the third pressure pulls the flexible inner part outward in order to form an interior space within the flexible inner part for the purpose of receiving the nipple (W), wherein the first and the at least one second pressure are applied in a further step in order to express milk.

5. The method as claimed in claim 1, wherein a negative pressure is used as the first pressure and a negative pressure and a positive pressure is used as the at least one second pressure.

6. The method as claimed in claim 1, wherein the first pressure and the at least one second pressure are used independently of one another.

7. The method as claimed in claim 1, wherein the first pressure and the at least one second pressure are applied in dependence on one another as stipulated by a control unit.

8. The method as claimed in claim 1, wherein there are at least two second chambers, which each have a second pressure applied to them independently of one another, wherein the ratio of the at least two second pressures relative to one another is varied over time.

9. The method as claimed in claim 1, wherein the first pressure and the at least one second pressure are applied at such a strength in the first and the at least one second chamber that the nipple (W) of the breast remains substantially unchanged in terms of length.

10. The method as claimed in claim 1, wherein a negative pressure is used as the first pressure and a negative pressure is used as the at least one second pressure.

11. The method as claimed in claim 1, wherein a negative pressure is used as the first pressure and a positive pressure is used as the at least one second pressure.

12. A method for operating a breastpump unit for expression of human breastmilk, wherein the breastpump unit has a vacuum pump for generating pressures and at least one breast shield for sealing application to a breast to be pumped, wherein the breast shield has a flexible inner part having an inner chamber for receiving a nipple (W) of the breast and at least one outer chamber which at least partially surrounds the nipple (W), wherein a first pressure is applied to the inner chamber by the vacuum pump and at least one second pressure is applied to the at least one outer chamber by the vacuum pump, the method including pressurizing the flexible inner part such that the latter fits on the nipple (W) in an annular manner in a first position and such that it frees the nipple (W) in the radial direction in a second position, wherein the first pressure pulsates and the at least one second pressure is substantially constant throughout a pumping session, wherein the breast shield has a flexible inner part which subdivides the breast shield into the inner chamber and the at least one outer chamber, and wherein the flexible inner part is subjected to the first pressure from the inside and to the at least one second pressure from the outside.

13. A breastpump unit for expression of human breastmilk, wherein the breastpump unit has a vacuum pump for generating pressures and at least one breast shield for sealing application to a breast to be pumped, wherein the breast shield has an inner chamber for receiving a nipple (W) of the breast and also at least one outer chamber which at least partially surrounds the nipple (W), wherein the inner chamber is configured to be subjected to a first pressure by the vacuum pump and the at least one outer chamber is configured to be subjected to at least one second pressure by the vacuum pump, wherein the first pressure is a substantially constant pressure throughout a pumping session and the at least one second pressure is a pulsating pressure, wherein at least one sensor is provided to determine the position of the nipple during the pumping operation, and wherein a controller is provided which is configured to vary the first pressure and the at least one second pressure in accordance with the determined position of the nipple.

14. The breastpump unit as claimed in claim 13, wherein the breast shield has a flexible inner part which subdivides the breast shield into the inner chamber and the at least one outer chamber, and wherein the flexible inner part is able to be subjected to the first pressure from the inside and to the at least one second pressure from the outside.

15. The breastpump unit as claimed in claim 13, wherein the breast shield has an outer breast shield body and a flexible inner part, wherein the flexible inner part
  forms an application region for sealing application to the human breast, and
  subdivides the breast shield into the inner chamber for receiving a nipple (W) of the breast and into the at least one outer chamber which at least partially surrounds the nipple (W),
  wherein the flexible inner part is configured in one piece and the breast shield has a further chamber in the form of a cavity which is subdivided by the at least one outer chamber,
  wherein a fixed or releasable connection between the flexible inner part and the breast shield body forms an encircling partition wall, and wherein the additional chamber is arranged in the application region of the breast shield.

16. The breastpump unit as claimed in claim 13, wherein at least one sensor is provided to determine the position of the nipple during the pumping operation, and wherein a controller is provided which is configured to vary the first pressure in accordance with this determined position of the nipple (W).

17. The breastpump unit as claimed in claim 13, wherein at least one sensor is provided to determine the position of the nipple during the pumping operation, and wherein a controller is provided which is configured to vary the at least one second pressure in accordance with this determined position of the nipple (W).

18. A breast shield of a breastpump unit for expression of human breastmilk, wherein the breastpump unit has a vacuum pump (200) for generating pressures, wherein the breast shield has:
  an application region for sealing application to the human breast, an inner chamber for receiving a nipple (W) of the breast, and at least one outer chamber which at least partially surrounds the nipple (W), wherein the inner chamber is configured to be subjected to a first pressure by the vacuum pump and the at least one outer chamber is configured to be subjected to at least one second pressure by the vacuum pump, wherein the first pressure is a pulsating pressure and the at least one second pressure is a substantially constant pressure throughout a pumping session, wherein the breast shield has a flexible inner part which subdivides the breast shield into the inner chamber and the at least one outer chamber, and wherein the flexible inner part is subjected to the first pressure from the inside and to the at least one second pressure from the outside.

19. The breast shield as claimed in claim 18, wherein the breast shield has a flexible inner part which subdivides the breast shield into the inner chamber and the at least one outer chamber, and wherein the flexible inner part is able to be subjected to the first pressure from the inside and to the at least one second pressure from the outside.

20. The breast shield as claimed in claim 19, wherein the flexible inner part is a flexible insert which is connected fixedly or releasably to a rigid or semirigid breast shield body.

* * * * *